United States Patent
Jang et al.

(10) Patent No.: US 10,674,951 B2
(45) Date of Patent: Jun. 9, 2020

(54) PORTABLE DEVICE FOR DETERMINING PHYSICAL STRENGTH OF A USER DURING EXERCISE

(71) Applicant: LG ELECTRONICS INC., Seoul (KR)

(72) Inventors: Seungjin Jang, Seoul (KR); Jungchae Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 105 days.

(21) Appl. No.: 15/741,091

(22) PCT Filed: Nov. 20, 2015

(86) PCT No.: PCT/KR2015/012559
§ 371 (c)(1),
(2) Date: Dec. 29, 2017

(87) PCT Pub. No.: WO2017/003045
PCT Pub. Date: Jan. 5, 2017

(65) Prior Publication Data
US 2018/0192935 A1     Jul. 12, 2018

(30) Foreign Application Priority Data
Jun. 29, 2015  (KR) .......... 10-2015-0091900

(51) Int. Cl.
*A61B 5/22*      (2006.01)
*A61B 5/11*      (2006.01)
(Continued)

(52) U.S. Cl.
CPC ............ *A61B 5/224* (2013.01); *A61B 5/0205* (2013.01); *A61B 5/02438* (2013.01);
(Continued)

(58) Field of Classification Search
CPC ... A61B 5/224; A61B 5/0205; A61B 5/02438; A61B 5/1118; A61B 5/1122;
(Continued)

(56) References Cited

U.S. PATENT DOCUMENTS 4,688,573 A * 8/1987 Alt ..................... A61N 1/3655
607/21
5,615,685 A * 4/1997 Suga .................. A61B 5/02438
600/300

(Continued)

FOREIGN PATENT DOCUMENTS

JP          11128396        5/1999
KR         100545772    *  1/2006
(Continued)

OTHER PUBLICATIONS

PCT International Application No. PCT/KR2015/012559, International Search Report dated Mar. 21, 2016, 4 pages.

*Primary Examiner* — Harshad R Patel
*Assistant Examiner* — Nigel H Plumb
(74) *Attorney, Agent, or Firm* — Lee, Hong, Degerman, Kang & Waimey

(57) ABSTRACT

A portable device for evaluating a physical strength is disclosed. The portable device includes a first sensor for sensing walking of a user; a second sensor for sensing heartbeat of the user; and a controller for: measuring a walking speed of the user using a sensed result of the first sensor; measuring a heart rate of the user using a sensed result of the second sensor; and evaluating a physical strength of the user using the measured heart rate when the walking speed of the user is changed by a specific speed or more by comparing a virtual heart rate calculated using the walking speed of the user with the measured heart rate.

14 Claims, 23 Drawing Sheets

(51) Int. Cl.
*G16H 40/63* (2018.01)
*G16H 40/67* (2018.01)
*G16H 20/30* (2018.01)
*A61B 5/0205* (2006.01)
*A61B 5/024* (2006.01)
*A61B 5/00* (2006.01)

(52) U.S. Cl.
CPC ........... *A61B 5/1118* (2013.01); *A61B 5/1122* (2013.01); *A61B 5/1123* (2013.01); *A61B 5/222* (2013.01); *A61B 5/681* (2013.01); *A61B 5/7246* (2013.01); *A61B 5/7278* (2013.01); *A61B 5/7285* (2013.01); *G16H 20/30* (2018.01); *G16H 40/63* (2018.01); *G16H 40/67* (2018.01); *A61B 5/02405* (2013.01)

(58) Field of Classification Search
CPC ....... A61B 5/1123; A61B 5/222; A61B 5/681; A61B 5/7246; A61B 5/7278; A61B 5/7285; A61B 5/02405; A61B 8/02; A61B 5/024; A61B 5/11; A61B 5/112; G16H 20/30; G16H 40/63; A62B 5/22; A61H 2230/42; A63B 2230/42
See application file for complete search history.

(56) References Cited

U.S. PATENT DOCUMENTS

| | | | | |
|---|---|---|---|---|
| 2003/0176815 | A1* | 9/2003 | Baba | A61B 5/02438 600/595 |
| 2013/0162427 | A1* | 6/2013 | Dibenedetto | A63B 24/0062 340/539.12 |
| 2014/0213858 | A1* | 7/2014 | Presura | A61B 5/721 600/301 |
| 2014/0213920 | A1* | 7/2014 | Lee | A61B 5/222 600/509 |
| 2014/0275854 | A1* | 9/2014 | Venkatraman | A61B 5/721 600/301 |
| 2014/0288390 | A1* | 9/2014 | Hong | A61B 5/02427 600/301 |
| 2016/0324432 | A1* | 11/2016 | Ahmed | A61B 5/0022 |
| 2017/0202486 | A1* | 7/2017 | Martikka | A61B 5/1118 |

FOREIGN PATENT DOCUMENTS

| | | | |
|---|---|---|---|
| KR | 1020080014614 | | 2/2008 |
| KR | 1020080110209 | | 12/2008 |
| KR | 1020100062735 | * | 6/2010 |

* cited by examiner

FIG. 9A

[EXERCISE EFFECTS AND LEVEL ACCORDING TO EXERCISE LEVEL]

| Fitness Target Zones: Heart Rates | | | |
|---|---|---|---|
| Exercise Level | Benefits | Intensity Level (Max HR %) | |
| Light Exercise | Healthy Heart Maintenance | 50% - 60% | ~911 |
| Weight Loss | Burn Fat & Calories | 60% - 70% | ~912 |
| Base-Aerobic | Increase stamina & endurance | 70% - 80% | ~913 |
| Conditioning | Fitness conditioning, muscle building, and athletic training | 80% - 90% | ~914 |
| Athletic-elite | Athletic training and endurance | 90% - 100% | ~915 |

FIG. 9E
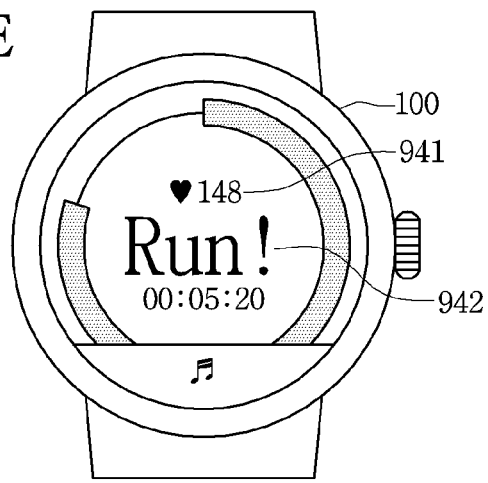
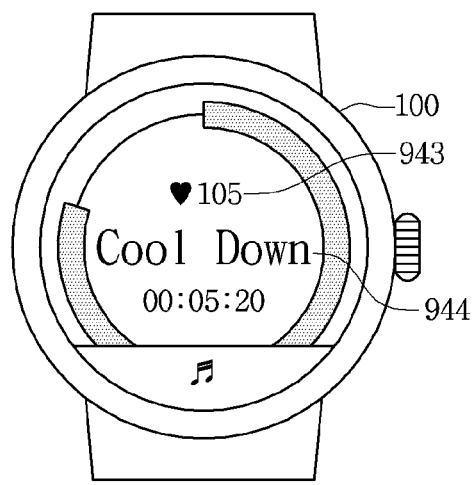
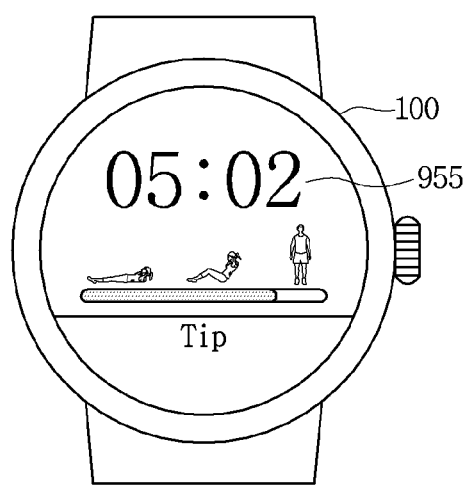

PORTABLE DEVICE FOR DETERMINING PHYSICAL STRENGTH OF A USER DURING EXERCISE

CROSS-REFERENCE TO RELATED APPLICATIONS

This application is the National Stage filing under 35 U.S.C. 371 of International Application No. PCT/KR2015/012559, filed on Nov. 20, 2015, which claims the benefit of earlier filing date and right of priority to Korean Application No. 10-2015-0091900, filed on Jun. 29, 2015, the contents of which are all hereby incorporated by reference herein in its entirety.

TECHNICAL FIELD

The present invention relates to a portable device for determining whether walking of a user of the portable device satisfies a specific condition and automatically evaluating the physical strength of the user, and a physical strength evaluation method thereof.

BACKGROUND ART

Cardiovascular endurance refers to aerobic exercise ability and a representative index indicating cardiovascular endurance is maximum oxygen consumption (VO2 Max). Maximum oxygen consumption (VO2 Max) may be measured by analyzing inspired gas and expired gas after graded maximal exercise and directly measuring oxygen consumption or evaluated by measuring a heart rate of a user during, before or after exercise of the user and estimating maximum oxygen consumption proportional to the heart rate.

Meanwhile, an existing cardiovascular endurance evaluation method has constraints such as cost problems caused by requirement of a long measurement time and specific equipments and facilities, or requirement of high exercise intensity.

For example, the existing cardiovascular endurance evaluation method requires expensive equipments for measuring the blood pressure, oxygen consumption, heart rate, breathing rate, lung capacity, ventilation, etc. of a user, sporting equipments (cycle, etc.) or exercise places (stairs, a sports field, etc.) for evaluating cardiovascular endurance, and requirement of high exercise intensity of a person to be measured, such as dead run by a predetermined distance for a predetermined time.

In addition, for example, as the existing cardiovascular endurance evaluation method, in Minute YMCA step test, a step having a height of 30.5 cm is used, 24 steps per minute is taken and the heart rate of a person to be measured should start to be measured within 5 seconds after exercise and should be measured for 1 minute. That is, since the user takes exercise satisfying a predetermined condition, cardiovascular endurance evaluation cannot be easily performed.

DISCLOSURE

Technical Problem

An object of the present invention is to provide a portable device for determining whether walking of a user of the portable device satisfies a specific condition and automatically evaluating the physical strength of the user, and a physical strength evaluation method thereof.

Technical Solution

A physical strength evaluation method of a portable device according to an embodiment of the present invention includes measuring a walking speed of a user, measuring a heart rate of the user, and evaluating a physical strength of the user using the measured heart rate when the walking speed of the user is changed by a specific speed or more.

A portable device according to an embodiment of the present invention includes a first sensor for sensing walking of a user, a second sensor for sensing heartbeat of the user, and a controller for measuring a walking speed of the user using a sensed result of the first sensor, measuring a heart rate of the user using a sensed result of the second sensor, and evaluating a physical strength of the user using the measured heart rate when the walking speed of the user is changed by a specific speed or more.

A physical strength evaluation method of a portable device communicating with a wearable device includes receiving a first sensed result of sensing walking of a user from the wearable device, receiving a second sensed result of sensing heartbeat of the user from the wearable device, and a controller measuring a walking speed of the user using the first sensed result, measuring a heart rate of the user using the second sensed result and evaluating a physical strength of the user using the measured heart rate when the walking speed of the user is changed by a specific speed or more.

Advantageous Effect

According to the present invention, it is possible to solve inconvenience of a user who takes exercise using specific equipments at a specific place under a specific condition, in order to evaluate the physical strength thereof.

DESCRIPTION OF DRAWINGS

FIGS. 9a to 9e are diagrams illustrating a method of outputting an exercise guide suitable for the physical strength of a user.

BEST MODE

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

Figure 1:
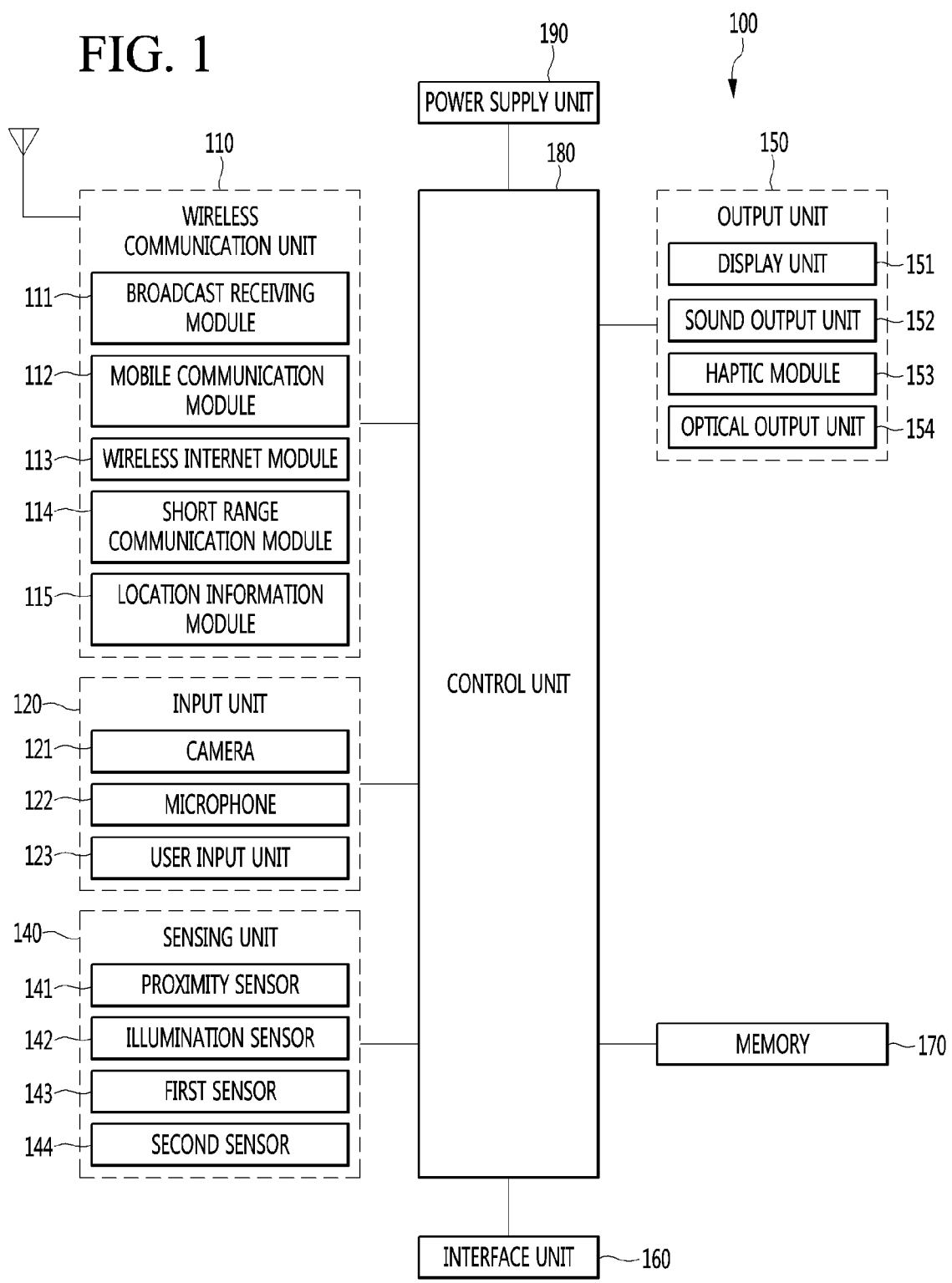
FIG. 1 is a block diagram illustrating a portable device related to the present invention.

FIG. 1 is a block diagram illustrating a portable device related to the present invention.

In the present embodiment, for example, a mobile terminal will be described as a portable device.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented. Referring now to FIG. 1, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks.

To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the various components depicted in FIG. 1A, or activating application programs stored in the memory 170. As one example, the controller 180 controls some or all of the components illustrated in FIG. 1 according to the execution of an application program that have been stored in the memory 170. The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

Some of the components may cooperatively operate in order to implement operation, control or control methods of the mobile terminal according to the below-described embodiments. In addition, operation, control or control methods of the mobile terminal may be implemented on the mobile terminal by executing at least one application program stored in the memory 170.

Prior to various embodiments implemented through the mobile terminal 100, the above-described various components will now be described in more detail with reference to FIG. 1.

Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like).

Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

The short-range communication module 114 may sense (or recognize) another mobile terminal, which is capable of performing communication and is located near the mobile terminal 100. Further, the controller 180 may transmit at least a part of data processed by the mobile terminal 100 to the other mobile terminal through the short-range communication module 114, when the other mobile terminal is authenticated to communicate with the mobile terminal 100 according to the present invention. Accordingly, the user of the other mobile terminal may use the data processed by the mobile terminal 100 through the other mobile terminal. For example, when the user receives a phone call through the mobile terminal 100, the user may have phone conversation through the other mobile terminal. When a message is received through the mobile terminal 100, the user may check the received message through the other mobile terminal.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal. As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 120. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like). In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

In some embodiments, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

The sensing unit 140 may include a first sensor 143.

The first sensor 143 may sense walking of the user. Specifically, when the user walks in a state of carrying the mobile terminal 100, the first sensor 143 may sense movement of the mobile terminal and output a signal corresponding to the movement of the mobile terminal to the controller 180. The controller 180 may detect information related to movement, such as the movement direction, movement angle, movement speed, intensity, current position, rotation direction, rotation angle, etc. of the mobile terminal from the signal generated by the first sensor 143.

The first sensor 143 may include various sensing units such as a gravity sensor, a geomagnetic sensor, an acceleration sensor, a tilt sensor, an altitude sensor, a depth sensor, a gyroscope sensor, an angular velocity sensor and a GPS sensor.

Meanwhile, the mobile terminal 100 may include a second sensor 144. The second sensor 144 may sense the heartbeat of the user. Specifically, in a state in which the user carries the mobile terminal 100, the second sensor 144 may sense the heartbeat of the user and output a signal corresponding to the heartbeat of the user to the controller 180.

To this end, the second sensor 144 may include a plus/minus electrode (not shown) contacting the body of the user, a detector (not shown) for detecting a heartbeat signal from the electrode, an amplifier (not shown) for amplifying the heartbeat signal detected by the detector, and a transmitter (not shown) for transmitting the amplified signal to the controller 180.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

A communication system which is operable with the variously described mobile terminals will now be described in more detail.

Such a communication system may be configured to utilize any of a variety of different air interfaces and/or physical layers. Examples of such air interfaces utilized by the communication system include Frequency Division Multiple Access (FDMA), Time Division Multiple Access (TDMA), Code Division Multiple Access (CDMA), Universal Mobile Telecommunications System (UMTS) (including, Long Term Evolution (LTE), LTE-A (Long Term Evolution-Advanced)), Global System for Mobile Communications (GSM), and the like.

By way of a non-limiting example only, further description will relate to a CDMA communication system, but such teachings apply equally to other system types including a CDMA wireless communication system as well as OFDM (Orthogonal Frequency Division Multiplexing) wireless communication system.

A CDMA wireless communication system generally includes one or more mobile terminals (MT or User Equipment, UE) 100, one or more base stations (BSs, NodeB, or evolved NodeB), one or more base station controllers (BSCs), and a mobile switching center (MSC). The MSC is configured to interface with a conventional Public Switched Telephone Network (PSTN) and the BSCs. The BSCs are coupled to the base stations via backhaul lines. The backhaul lines may be configured in accordance with any of several known interfaces including, for example, E1/T1, ATM, IP, PPP, Frame Relay, HDSL, ADSL, or xDSL. Hence, the plurality of BSCs can be included in the CDMA wireless communication system.

Each base station may include one or more sectors, each sector having an omni-directional antenna or an antenna pointed in a particular direction radially away from the base station. Alternatively, each sector may include two or more different antennas. Each base station may be configured to support a plurality of frequency assignments, with each frequency assignment having a particular spectrum (e.g., 1.25 MHz, 5 MHz, etc.).

The intersection of sector and frequency assignment may be referred to as a CDMA channel. The base stations may also be referred to as Base Station Transceiver Subsystems (BTSs). In some cases, the term "base station" may be used to refer collectively to a BSC, and one or more base stations. The base stations may also be denoted as "cell sites." Alternatively, individual sectors of a given base station may be referred to as cell sites.

A broadcasting transmitter (BT) transmits a broadcast signal to the mobile terminals 100 operating within the system. The broadcast receiving module 111 of FIG. 1A is typically configured inside the mobile terminal 100 to receive broadcast signals transmitted by the BT.

Global Positioning System (GPS) satellites for locating the position of the mobile terminal 100, for example, may cooperate with the CDMA wireless communication system. Useful position information may be obtained with greater or fewer satellites than two satellites. It is to be appreciated that other types of position detection technology, (i.e., location technology that may be used in addition to or instead of GPS location technology) may alternatively be implemented. If desired, at least one of the GPS satellites may alternatively or additionally be configured to provide satellite DMB transmissions.

The location information module 115 is generally configured to detect, calculate, or otherwise identify a position of the mobile terminal. As an example, the location information module 115 may include a Global Position System (GPS) module, a Wi-Fi module, or both. If desired, the location information module 115 may alternatively or additionally function with any of the other modules of the wireless communication unit 110 to obtain data related to the position of the mobile terminal.

A typical GPS module 115 can measure an accurate time and distance from three or more satellites, and accurately calculate a current location of the mobile terminal according to trigonometry based on the measured time and distances. A method of acquiring distance and time information from three satellites and performing error correction with a single satellite may be used. In particular, the GPS module may acquire an accurate time together with three-dimensional speed information as well as the location of the latitude, longitude and altitude values from the location information received from the satellites. Furthermore, the GPS module can acquire speed information in real time to calculate a current position. Sometimes, accuracy of a measured position may be compromised when the mobile terminal is located in a blind spot of satellite signals, such as being located in an indoor space. In order to minimize the effect of such blind spots, an alternative or supplemental location technique, such as Wi-Fi Positioning System (WPS), may be utilized.

The Wi-Fi positioning system (WPS) refers to a location determination technology based on a wireless local area network (WLAN) using Wi-Fi as a technology for tracking the location of the mobile terminal 100. This technology typically includes the use of a Wi-Fi module in the mobile terminal 100 and a wireless access point for communicating with the Wi-Fi module.

The Wi-Fi positioning system may include a Wi-Fi location determination server, a mobile terminal, a wireless access point (AP) connected to the mobile terminal, and a database stored with wireless AP information.

The mobile terminal connected to the wireless AP may transmit a location information request message to the Wi-Fi location determination server.

The Wi-Fi location determination server extracts the information of the wireless AP connected to the mobile terminal 100, based on the location information request message (or signal) of the mobile terminal 100. The information of the wireless AP may be transmitted to the Wi-Fi location determination server through the mobile terminal 100, or may be transmitted to the Wi-Fi location determination server from the wireless AP.

The information of the wireless AP extracted based on the location information request message of the mobile terminal 100 may include one or more of media access control (MAC) address, service set identification (SSID), received signal strength indicator (RSSI), reference signal received Power (RSRP), reference signal received quality (RSRQ), channel information, privacy, network type, signal strength, noise strength, and the like.

The Wi-Fi location determination server may receive the information of the wireless AP connected to the mobile terminal 100 as described above, and may extract wireless AP information corresponding to the wireless AP connected to the mobile terminal from the pre-established database. The information of any wireless APs stored in the database may be information such as MAC address, SSID, RSSI, channel information, privacy, network type, latitude and longitude coordinate, building at which the wireless AP is located, floor number, detailed indoor location information (GPS coordinate available), AP owner's address, phone number, and the like. In order to remove wireless APs provided using a mobile AP or an illegal MAC address during a location determining process, the Wi-Fi location determination server may extract only a predetermined number of wireless AP information in order of high RSSI.

Then, the Wi-Fi location determination server may extract (analyze) location information of the mobile terminal 100 using at least one wireless AP information extracted from the database.

A method for extracting (analyzing) location information of the mobile terminal 100 may include a Cell-ID method, a fingerprint method, a trigonometry method, a landmark method, and the like.

The Cell-ID method is used to determine a position of a wireless AP having the largest signal strength, among peripheral wireless AP information collected by a mobile terminal, as a position of the mobile terminal. The Cell-ID method is an implementation that is minimally complex, does not require additional costs, and location information can be rapidly acquired. However, in the Cell-ID method, the precision of positioning may fall below a desired threshold when the installation density of wireless APs is low.

The fingerprint method is used to collect signal strength information by selecting a reference position from a service area, and to track a position of a mobile terminal using the signal strength information transmitted from the mobile terminal based on the collected information. In order to use the fingerprint method, it is common for the characteristics of radio signals to be pre-stored in the form of a database.

The trigonometry method is used to calculate a position of a mobile terminal based on a distance between coordinates of at least three wireless APs and the mobile terminal. In order to measure the distance between the mobile terminal and the wireless APs, signal strength may be converted into distance information, Time of Arrival (ToA), Time Difference of Arrival (TDoA), Angle of Arrival (AoA), or the like may be taken for transmitted wireless signals.

The landmark method is used to measure a position of a mobile terminal using a known landmark transmitter.

In addition to these position location methods, various algorithms may be used to extract (analyze) location information of a mobile terminal.

Such extracted location information may be transmitted to the mobile terminal 100 through the Wi-Fi location determination server, thereby acquiring location information of the mobile terminal 100.

The mobile terminal 100 can acquire location information by being connected to at least one wireless AP. The number of wireless APs required to acquire location information of the mobile terminal 100 may be variously changed according to a wireless communication environment within which the mobile terminal 100 is positioned.

Various embodiments described herein may be implemented in a computer-readable medium or similar medium using, for example, software, hardware, or any combination thereof.

Meanwhile, although a mobile terminal is described as a portable device in the present embodiment, the present invention is not limited thereto and all portable devices capable of measuring the walking speed and heart rate of a user to evaluate the physical strength of the user may be used.

In addition, the portable device may be a wearable device and the portable device may be a watch-type mobile terminal among wearable devices. An embodiment in which a wearable device is implemented as a portable device will be described with reference to FIG. 2.

Figure 2:
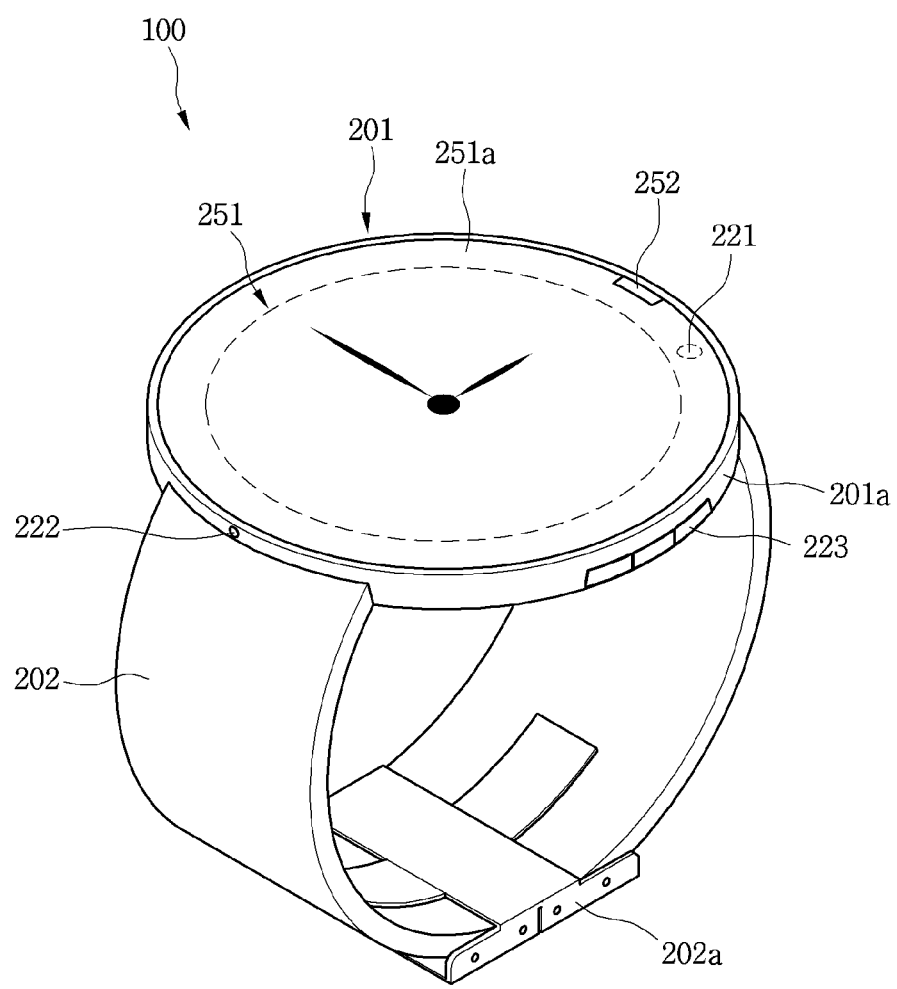
FIG. 2 is a perspective view showing an example of a watch-type mobile terminal related to the present invention.

FIG. 2 is a perspective view showing an example of a watch-type mobile terminal related to the present invention.

The watch-type mobile terminal 100 shown in FIG. 2 may include all the components shown in FIG. 1.

Although the display 251 of the watch-type mobile terminal 100 shown in FIG. 2 has a circular shape, the present invention is not limited thereto and the display may have an elliptical shape or a rectangular shape. The display 251 of the present invention may have any shape capable of providing a visually good image to a user and aiding the user in manipulation of a touchscreen thereof.

Referring to FIG. 2, the watch-type mobile terminal 100 includes a main body 201 including the display 251 and a band 202 connected to the main body 201 and capable of being worn over a wrist of the user. The display 251 may correspond to a touchscreen.

The main body 201 may include a case having a certain appearance. As illustrated, the case may include a first case 201a and a second case 201b cooperatively defining an inner space for accommodating various electronic components. Other configurations are possible. For instance, a single case may alternatively be implemented, with such a case being configured to define the inner space, thereby implementing a mobile terminal 100 with a uni-body.

The watch-type mobile terminal 100 can perform wireless communication, and an antenna for the wireless communication can be installed in the main body 201. The antenna may extend its function using the case. For example, a case including a conductive material may be electrically connected to the antenna to extend a ground area or a radiation area.

The display unit 251 is shown located at the front side of the main body 201 so that displayed information is viewable to a user. In some embodiments, the display unit 351 includes a touch sensor so that the display unit can function as a touch screen. As illustrated, window 351a is positioned on the first case 201a to form a front surface of the terminal body together with the first case 201a.

The illustrated embodiment includes audio output module 252, a camera 221, a microphone 222, and a user input unit 223 positioned on the main body 201. When the display unit 251 is implemented as a touch screen, additional function keys may be minimized or eliminated. For example, when the touch screen is implemented, the user input unit 223 may be omitted.

The band 202 is commonly worn on the user's wrist and may be made of a flexible material for facilitating wearing of the device. As one example, the band 202 may be made of fur, rubber, silicon, synthetic resin, or the like. The band 202 may also be configured to be detachable from the main body 201. Accordingly, the band 202 may be replaceable with various types of bands according to a user's preference.

In one configuration, the band 202 may be used for extending the performance of the antenna. For example, the band may include therein a ground extending portion (not shown) electrically connected to the antenna to extend a ground area.

The band 202 may include fastener 302a. The fastener 202a may be implemented into a buckle type, a snap-fit hook structure, a Velcro® type, or the like, and include a flexible section or material. The drawing illustrates an example that the fastener 202a is implemented using a buckle.

Figure 3:
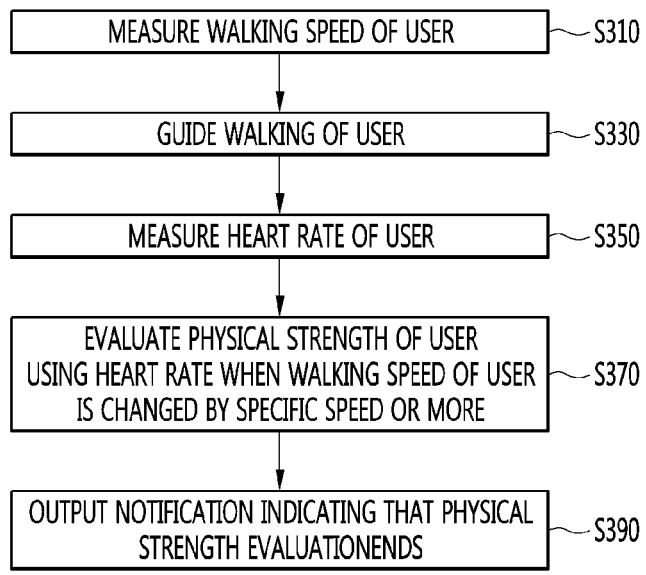
FIG. 3 is a flowchart illustrating a physical strength evaluation method of a portable device according to an embodiment of the present invention.

FIG. 3 is a flowchart illustrating a physical strength evaluation method of a portable device according to an embodiment of the present invention.

In FIG. 3, the physical strength evaluation method of the portable device according to the embodiment of the present invention may include measuring a walking speed of a user (S310), outputting information for guiding walking of the user when walking of the user does not satisfy a criterion for evaluating the physical strength of the user (S330), measuring a heart rate of the user (S350), evaluating the physical strength of the user using the measured heart rate when the walking speed of the user is changed by a specific speed or more (S370), and outputting information indicating that physical strength evaluation of the user ends (S390).

In the physical strength evaluation method of the portable device, in association with step S310 of measuring the walking speed of the user, the controller 180 may measure the walking speed of the user using the sensed result of the first sensor 143. Specifically, the first sensor 143 may sense walking of the user. In addition, the controller 180 may receive the sensed result from the first sensor 143 and measure the walking speed of the user. Here, walking refers to movement of the body of the user by consecutive movement of joints and muscles of the user of the mobile terminal 100 and may include walking or running by movement of joints and muscles.

Meanwhile, the term "walking speed" used in the present invention may mean a "movement distance per unit time according to walking of the user". Alternatively, the term "walking speed" used in the present invention may mean the number of steps of user per unit time". The number of steps of the user per unit time may be calculated using at least one of a walking period of the user, the number of samples detected per step of the user and the number of steps of the user measured for a specific time. A detailed method of calculating the walking speed will be described below with reference to FIG. 6b.

A detailed method of measuring the walking speed of the user will be described with reference to FIG. 4.

Figure 4A:
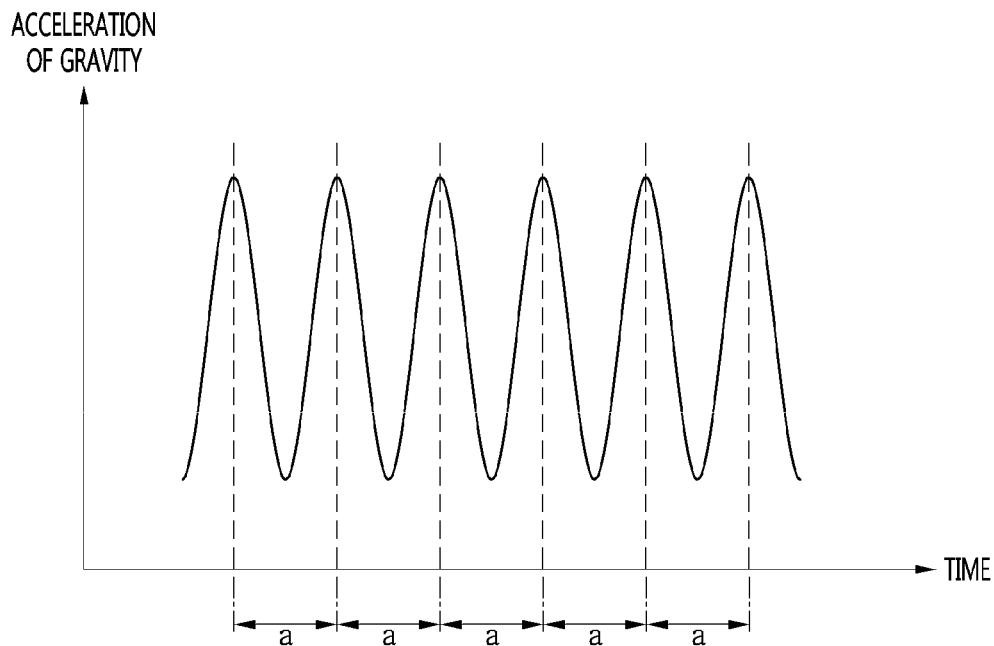
FIGS. 4a and 4b are diagrams illustrating a method of measuring a walking speed of a user by measuring acceleration of gravity when the user walks, according to an embodiment of the present invention.
Figure 4B:
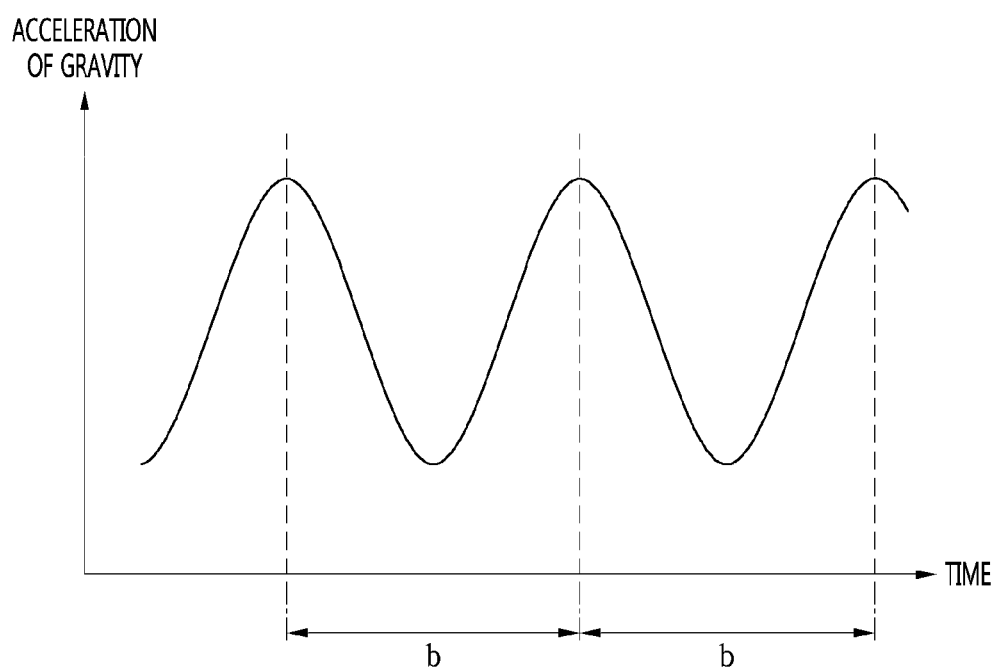

FIG. 4 is a diagram illustrating a method of measuring a walking speed of a user by measuring acceleration of gravity when the user walks.

The first sensor 143 may sense walking of the user through change in acceleration of gravity. In addition, the first sensor 143 may transmit the sensed result to the controller 180.

FIG. 4a is a diagram showing change in acceleration of gravity according to walking of a user.

It can be seen from FIG. 4a that acceleration of gravity measured by a portable device 100 of a user is changed according to walking of the user. In this case, one period a of the acceleration-of-gravity change graph may mean that the user takes a step forward. Since it is assumed that the user moves at a constant speed in the present embodiment, it can be seen from FIG. 4a that the period a per step of the user is constant.

The controller 180 may measure the movement speed according to walking of the user. Specifically, the sensing unit 140 may sense that movement of the user is walking and the movement distance of the user, and the controller 180 may measure the movement distance according to walking of the user using the sensed result of the sensing unit 140. In addition, the controller 180 may measure the movement speed according to walking of the user using the movement distance of the user and a time required therefor. For example, when walking of the user is sensed by the sensing unit 140 and the user has moved by 20 m for 10 seconds, the walking speed of the user may be 2 m/s. In addition, the controller 180 may continuously measure and compare the walking speed of the user, thereby sensing change in walking speed of the user.

In addition, the controller 180 may measure the walking speed of the user using the time information of one period a, that is, the time a required for the user to take a step forward. Specifically, the controller 180 may sense the movement distance of the user who takes a step forward and measure a speed equation (speed=distance/time). For example, if the user has taken a step forward for 0.5 seconds and the movement distance of the user per step is 0.55 m, the walking speed of the user may be 1.1 m/s. As another example, if the user has taken 10 steps for 5 seconds and the movement distance of the user per step is 0.55 m, the walking speed of the user may be 1.1 m/s.

In addition, the controller 180 may measure change in walking speed of the user using change in walking period of the user.

For example, the controller 180 may measure the walking period of the user by measuring a time required for the user to take a step forward. In addition, the controller 180 measure a time required for the user to take two or more steps and calculate an average thereof, thereby measuring the walking period of the user. In addition, the controller 180 may measure change in walking speed of the user using information on change in walking period of the user. For example, if the walking period of the user is changed from 0.6 seconds to 0.3 seconds, the controller 180 may determine that the walking speed of the user has been changed using the walking period of the user changed from 0.6 seconds to 0.3 seconds.

As another example, when the walking period of the user is measured according to the number of samples detected per specific time unit, the controller 180 may measure the walking period of the user using the number of samples acquired per step of the user. In addition, the controller 180 may calculate an average of the number of samples acquired by two or more steps of the user, thereby measuring the walking period of the user. For example, when the time unit of one sample may be 0.05 seconds (that is, the frequency of the sample is 20 Hz) and 60 samples are detected for 5 steps, the walking period of the user may be 0.6 seconds. In addition, when the user changes the walking speed and 30 samples are detected for 5 steps, the walking period of the user may be 0.3 seconds. In this case, the controller 180 may determine that the walking period of the user is changed using the walking period of the user changed from 0.6 seconds to 0.3 seconds. In addition, the controller 180 may determine that the walking speed of the user is changed using the average number of samples detected per step of the user changed from 12 to 6.

In addition, the controller 180 may measure change in walking speed of the user using change in number of steps of the user measured for a specific time. For example, when the walking speed of the user is changed in a state in which the number of steps of the user is 10 for 5 seconds such that the number of steps of the user becomes 20, the controller 180 may measure change in walking speed of the user using the number of steps of the user for 5 seconds changed from 10 to 20.

Referring to FIG. 3 again, the physical strength evaluation method of the portable device according to the embodiment of the present invention may include step S330 of outputting information for guiding walking of the user when walking of the user does not satisfies the criterion for evaluating the physical strength of the user.

Figure 5A:
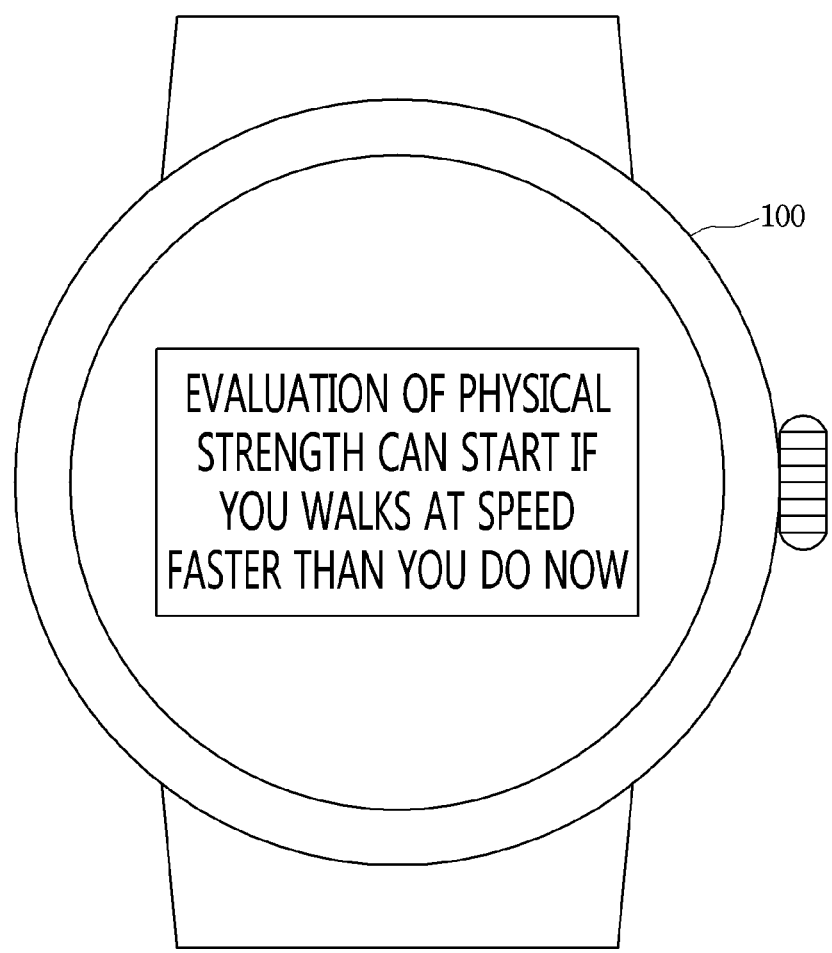
FIGS. 5a and 5b are diagrams illustrating a method of outputting information for guiding walking of a user according to an embodiment of the present invention.

Here, the criterion for evaluating the physical strength of the user may be change in walking speed of the user by a specific speed or more. Specifically, when the user changes the walking speed thereof, the heart rate of the user is also changed. When the walking speed of the user is changed by the specific speed or more, change in heart rate of the user is large and thus evaluation accuracy of the physical strength of the user can be improved. Accordingly, as shown in FIG. 5*a*, the controller 180 may output information for leading the user to change the walking speed of the user by a specific speed. Here, the specific speed may be a minimum speed changed to evaluate the physical strength of the user using change in heart rate of the user.

In addition, the criterion for evaluating the physical strength of the user may be maintenance of the walking speed of the user at a constant speed. Specifically, accuracy of physical strength evaluation of the user can be improved when the user changes the walking speed thereof by a specific speed and then measures change in heart rate while maintaining the changed speed. Accordingly, as shown in FIG. 5*b*, the controller 180 may output information for leading the user to maintain a changed speed in a state in which the user changes the walking speed thereof by a specific speed or more.

In addition, the criterion for evaluating the physical strength of the user may be passage of a specific time in a state in which the walking speed of the user is maintained at a constant speed. Here, the specific time may be a minimum time when the physical strength of the user can be evaluated using the heart rate of the user. Specifically, in order to enable the user to maintain the walking speed thereof at a constant speed for the minimum time when the physical strength of the user can be evaluated, the controller 180 may output information for leading the user to maintain the current walking speed of the user for a specific time, as shown in FIG. 5*b*.

Figure 5B:
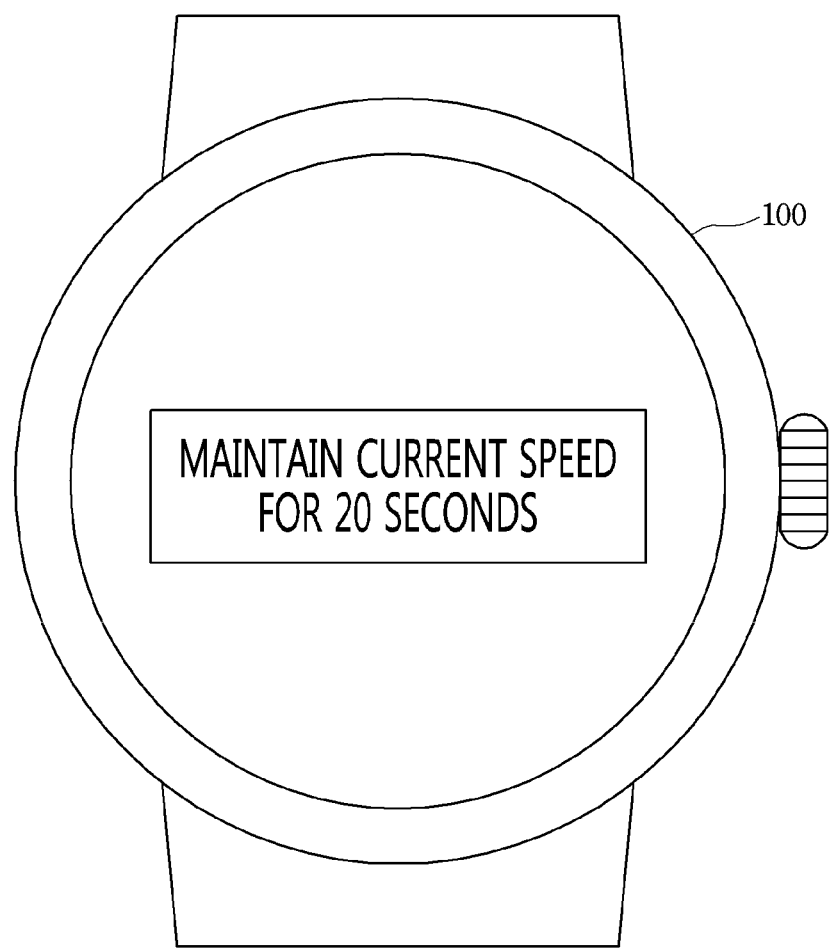

Meanwhile, the controller 180 may control the display 151 to output a guide information as an image, as shown in FIGS. 5*a* and 5*b*. The present invention is not limited thereto and the controller 180 may control the audio output module 152 to audibly output the guide information. In addition, the controller 180 may deliver the guide information to the user using a flickering signal through the optical output module 154 and tactile effects through the haptic module 153.

Meanwhile, although the user is guided such that walking of the user satisfies the criterion for evaluating the physical strength of the user and the physical strength of the user is evaluated when walking of the user satisfies the criterion for evaluating the physical strength of the user in the present embodiment, the present invention is not limited thereto. For example, the portable device 100 may automatically evaluate the physical strength of the user when walking of the user satisfies the criterion for evaluating the physical strength of the user, without guiding the user.

Specifically, the controller 180 may evaluate the physical strength of the user using the heart rate of the user, when the walking speed of the user is changed by the predetermined speed or more. For example, the first sensing unit 143 may continuously sense walking of the user and transmit the sensed result to the controller 180, and the controller 180 may measure the walking speed of the user using the sensed result received from the first sensing unit 143 and start to evaluate the physical strength of the user using the heart rate of the user when the walking speed of the user is changed by the specific speed or more.

In addition, the controller 180 may evaluate the physical strength of the user using the heart rate of the user, when the user maintains the walking speed thereof after the walking speed of the user is changed by the specific speed. In addition, the controller 180 may evaluate the physical strength of the user using the heart rate of the user, when the user maintains the changed walking speed at a constant speed for a first time.

Here, the first time may be predetermined and may be a minimum time when the physical strength of the user can be evaluated using the heart rate of the user or an ideal time when the physical strength of the user can be evaluated using the heart rate of the user.

The mobile terminal according to the embodiment of the present invention may automatically evaluate the physical strength of the user when walking of the user satisfies a predetermined condition, thereby solving inconvenience of the user who takes exercise under a specific condition using specific equipments at a specific place in order to evaluate the physical strength of the user.

Referring to FIG. 3 again, the physical strength evaluation method of the portable device according to the embodiment of the present invention may include step S350 of measuring the heartbeat of the user. Specifically, the second sensor 144 may sense the heart rate of the user, and the controller 180 may measure the heart rate of the user using the sensed result of the second sensor 144.

Meanwhile, the physical strength evaluation method of the portable device according to the embodiment of the present invention may include step S370 of evaluating the physical strength of the user using the measured heart rate when the walking speed of the user is changed by the specific speed or more.

This will be described in greater detail with reference to FIG. 6.

FIG. 6 is a diagram showing the result of measuring the heart rate of the user according to one embodiment of the present invention.

Figure 6A:
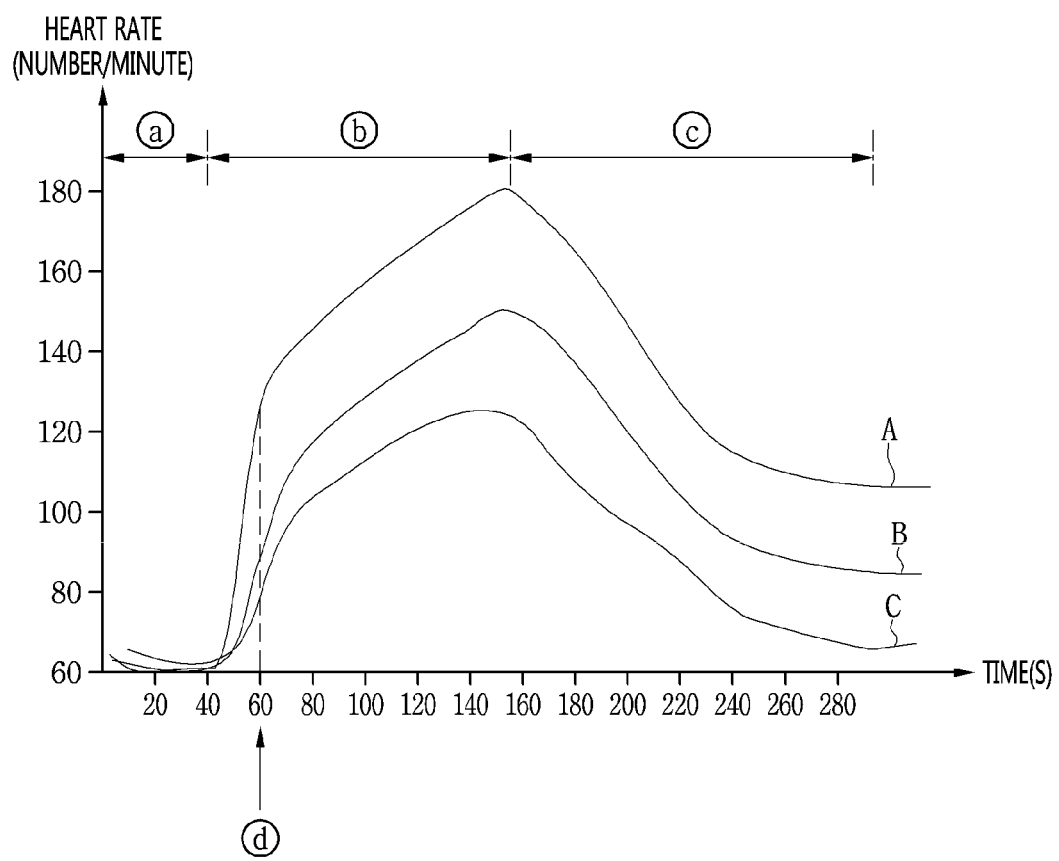
FIGS. 6a and 6b are diagrams illustrating a result of measuring the heart rate of a user according to an embodiment of the present invention.

In FIG. 6a, a period ⓐ is a warming-up period. The warming-up period refers to a period in which the user does not walk or slowly walks such that the heart rate thereof is stable. In this period, the heart rates of users A, B and C are all in a range of 60 to 70 (number/minute), which is the normal range of an adult. Assume that the walking speed of the user in the period ⓐ is 0.56 m/s.

A period ⓑ refers to a period in which the walking speed of the user is increased and then is maintained at a constant speed. In the present embodiment, assume that the walking speed in the period ⓑ is 1.94 m/s.

The controller 180 may evaluate the physical strength of the user using the measured heart rate, when the walking speed of the user is changed by the specific speed or more. For example, when specific speed change for evaluating the physical strength of the user is 1 m/s, in the present embodiment, since the walking speed of the user is increased from 0.56 m/s (period ⓐ) to 1.94 m/s (period ⓑ), the controller 180 may measure the physical strength of the user using the measured heart rate.

Meanwhile, the controller 180 may determine whether the walking speed of the user is changed by the specific speed or more using information on the walking period of the user, as described with reference to FIG. 4. For example, in the case where the walking speed of the user is set to be changed by the specific speed or more when the time required for the user to take one step forward is changed by 0.2 seconds or more, if the time required to take one step forward in the period ⓐ is 0.6 seconds and the time required to take one step forward in the period ⓑ is 0.3 seconds, the controller 180 may determine that the walking speed of the user is changed by the specific speed or more. In addition, since the walking speed of the user is changed by the specific speed or more, the controller 180 may evaluate the physical strength of the user using the heart rate.

As another example, the controller 180 may determine whether the walking speed of the user is changed by the specific speed or more using information on the number of samples detected per step of the user. For example, in the case where the walking speed of the user is set to be changed by the specific speed or more when the number of samples detected per step of the user is changed by 5 or more, if the number of samples detected per step in the period ⓐ is 12 and the number of samples detected per step in the period ⓑ is 6, the controller 180 may determine that the walking speed of the user is changed by the specific speed or more. In addition, since the walking speed of the user is changed by the specific sped or more, the controller 180 may evaluate the physical strength of the user using the heart rate.

In addition, the controller 180 may determine whether the walking speed of the user is changed by the specific speed or more using information on the number of steps of the user measured for a specific time. For example, in the case where the walking speed of the user is set to be changed by the specific speed or more when the number of steps of the user for 5 seconds is changed by 7 or more, if the number of steps of the user for 5 seconds in the period ⓐ is 10 and the number of steps of the user for 5 seconds in the period ⓑ is 20, the controller 180 may determine that the walking speed of the user is changed by the specific speed or more. In addition, since the walking speed of the user is changed by the specific sped or more, the controller 180 may evaluate the physical strength of the user using the heart rate.

A point ⓓ refers to a point where the slope of the heart-rate increasing curve is measured. The physical strength evaluation method of the portable device according to the present invention may evaluate the slope of the heart-rate change curve of the user, thereby evaluating the physical strength of the user.

Specifically, it can be seen that the heart rate of the user A is rapidly increased in the period ⓑ as compared to the user B and the user C. Since the heart rate of a person having bad cardiopulmonary capacity is rapidly increased by exercise, the cardiopulmonary capacity of the user A may be worse than those of the user B and the user C.

It can be seen that the heart rate of the user C is slowly increased in the period ⓑ as compared to the user A and the user B. Since the heart rate of a person having good cardiopulmonary capacity is slowly increased by exercise, the cardiopulmonary capacity of the user C may be better than those of the user A and the user B.

Meanwhile, the user B may have normal cardiopulmonary capacity.

The controller 180 may compare the slope of the heart-rate curve measured at the point ⓓ with the slope a specific heart-rate increasing curve obtained statistically under the same condition, thereby measuring the cardiopulmonary capacity of the user. For example, if the slope of the heart-rate curve measured at the point ⓓ of the user A is greater than that of the specific heart-rate increasing curve, the controller 180 may determine that the cardiopulmonary capacity of the user A is bad. As another example, if the slope of the heart-rate curve measured at the point ⓓ of the user B is equal or similar to that of the specific heart-rate increasing curve, the controller 180 may determine that the cardiopulmonary capacity of the user B is normal.

The controller 180 may evaluate the physical strength of the user using the slope of the heart rate of the user when a second time has passed after the walking speed of the user is changed by the specific speed. In the present embodiment, assume that the point of time when the second time has passed is the point ⓓ of FIG. 6.

Meanwhile, the second time may refer to a minimum time when the physical strength of the user can be evaluated using the measured heart rate of the user. Specifically, the second time may refer to a minimum time when the physical strength of the user can be evaluated using the slope of the heart-rate change curve of the user. For example, when the users increase the walking speeds thereof, the heart rates of the user A, the user B and the user C are rapidly increased. The heart rates of the user A, the user B and the user C are similarly increased immediately after the users increase the walking speeds thereof. Accordingly, the minimum time when the physical strength of the user can be evaluated may be a time from when the walking speed of the user is changed to when increments in heart rates of the users A, B and C start to become different from one another.

In this case, the controller 180 may output information indicating that physical strength evaluation of the user ends when the second time has passed, and evaluate the physical strength of the user.

Meanwhile, the controller 180 may evaluate the physical strength of the user using at least one of a maximum value and a minimum value of the heart rate measured for the first time after the walking speed of the user is changed by the specific speed or more. Here, the first time may refer to a time when at least one of the maximum value and the minimum value of the heart rate can be obtained under the same condition and may be statistically acquired and set as the default.

Specifically, the controller 180 may compare the maximum value of the heart rate obtained in the period ⓑ with the maximum value of the heart rate obtained statistically under the same condition, thereby measuring the cardiopulmonary capacity of the user. For example, when the maximum value of the heart rate obtained in the period ⓑ of the user A is greater than the maximum value of the heart rate obtained statistically under the same condition by a specific value or more, the controller 180 may determine that the cardiopulmonary capacity of the user A is bad. As another example, when the maximum value of the heart rate obtained in the period ⓑ of the user B is within a specific range of the maximum value of the heart rate obtained statistically under the same condition, the controller 180 may determine that the cardiopulmonary capacity of the user B is normal.

Meanwhile, the first time may refer to a time when the maximum value of the heart rate of the user may be estimated. Specifically, the first time may be a time from when the walking speed of the user is changed by the specific speed or more to when it may be determined where the maximum value of the heart rate of the user converges through analysis of increment of the heart rate of the user. If the walking speed of the user A is changed by the specific speed or more at 40 seconds, the controller 180 estimates the heart rate of the user as being increased to 195 at 100 seconds through analysis of the heart-rate increasing curve of the user, and the heart rate of the user is actually increased to 195 at 120 seconds, the first time may be 60 seconds obtained by subtracting 40 seconds from 100 seconds. Similarly, the first time may be a time when the minimum value of the heart rate of the user may be estimated.

In this case, the controller 180 may output information indicating that physical strength evaluation of the user ends when the first time has passed, and evaluate the physical strength of the user.

The period ⓒ refers to a period that the walking speed of the user is decreased again and then is maintained at a constant speed. In the present embodiment, assume that the walking speed in the period ⓒ is 1.12 m/s.

When the walking speed of the user is decreased by the specific speed or more, the controller 180 may evaluate the physical strength of the user using the measured heart rate. The method of evaluating the physical strength in the period ⓒ is similar to that of the period ⓑ, but is different therefrom in that decrement of the heart-rate curve or the minimum value of the heart rate is used. For example, the controller 180 may compare the slope of the heart-rate decreasing curve with the slope of the heart-rate decreasing curve obtained statistically under the same condition, thereby determining the recovery speed of the heart rate of the user. In addition, the controller 180 may compare the minimum value of the heart rate with the minimum value obtained statistically under the same condition, thereby determining the recovery speed of the heart rate of the user.

In addition, when the walking speed of the user is decreased, the controller 180 may evaluate the physical strength of the user using the recovery time of the heart rate. Specifically, when the walking speed of the user is decreased and thus the heart rate of the user is also decreased, the controller 180 may measure a time until the heart rate is decreased to the heart rate of the user before evaluation of the physical strength, thereby evaluating the physical strength of the user. For example, the controller 180 may measure a time until the heart rate of the user in the period ⓒ is decreased to the heart rate of the user in the period ⓐ, thereby evaluating the physical strength of the user. In this case, the recovery time of the heart rate of the user C is shorter than that of the user A, the controller 180 may determine that the physical strength of the user C is higher than that of the user A.

Figure 6B:
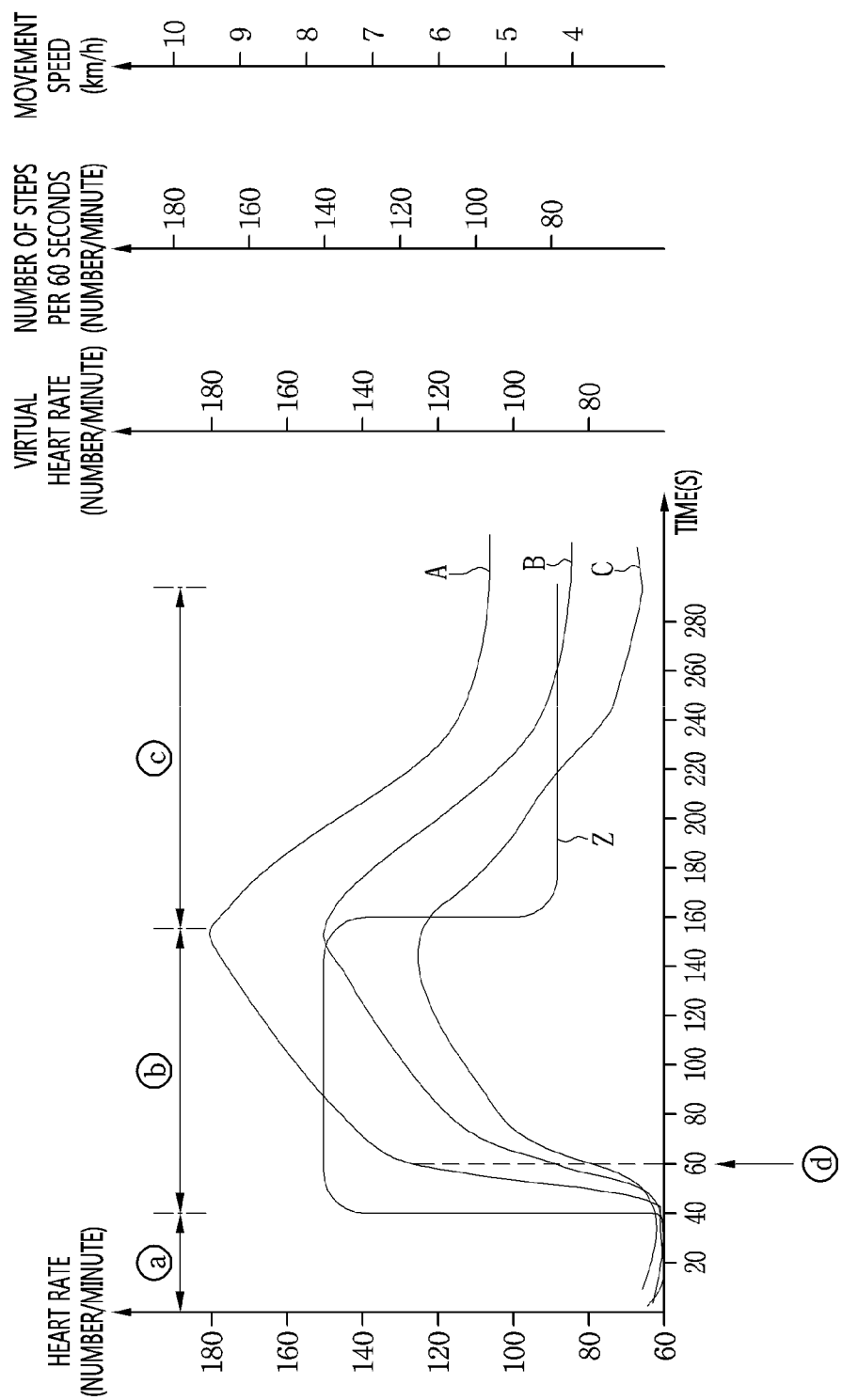

FIG. 6*b* is a diagram illustrating a method of comparing a virtual heart rate calculated using the walking speed of the user with the actual heart rate of the user to evaluate the physical strength of the user.

In FIG. 6*b*, a Z line may mean the movement speed of the user. That is, the heart rates of the users A, B and C may be changed according to change in movement speed of the user. In addition, even when the movement speeds of the users A, B and C are equally changed, since the physical strengths of the users A, B and C are different, the actual heart rates of the user A, B and C may be differently changed.

In addition, the Z line of FIG. 6*b* may mean the number of steps of the user per minute, that is, the number of steps of the user per 60 seconds. That is, the actual heart rates of the users A, B and C may be changed according to change in number of steps per unit time of the user. In addition, even when the numbers of steps per unit time of the users A, B and C are equally changed, since the physical strengths of the users A, B and C are different, the actual heart rates of the user A, B and C may be differently changed.

In addition, the Z line of FIG. 6*b* means the virtual heart rate calculated using the walking speed of the user. The controller 180 may calculate the virtual heart rate using the following equation.

$$\text{Virtual heart rate} = a(\text{constant}) * \text{the number of steps of the user/minute}$$

where, the term "number of steps of the user/minute" means the number of steps of the user per 60 seconds, and the walking speed of the user may be calculated by at least one of the walking period of the user, the number of samples detected per specific number of steps and the number of steps of the user detected for a specific time.

Specifically, the controller 180 may calculate the number of steps of the user per 60 seconds using the walking period of the user. For example, when a time required for the user to taking one step forward is 0.3 seconds, the number of steps of the user per 60 seconds may be calculated as 200.

In addition, the controller 180 may calculate the number of steps of the user per 60 seconds using the number of samples of a specific time unit detected per step. For example, if the time unit of one sample is 0.05 seconds (that is, the frequency of the sample is 20 Hz) and the number of samples detected per step of the user is 6, the controller 180 may calculate the number of steps of the user per 60 seconds as 200.

In addition, the controller 180 may calculate the number of steps of the user per 60 seconds using the number of steps of the user measured for a specific time. For example, if the number of steps of the user for 5 seconds is 20, the controller 180 may calculate the number of steps of the user per 60 seconds as 240.

Meanwhile, as described with reference to FIG. 4, the walking period of the user may be calculated by the average of the time required for a plurality of steps and the number of samples detected per step may be calculated by the average of the number of samples detected during a plurality of steps.

Meanwhile, a (constant) may be a value changed according to the properties of the user. Specifically, the portable device 100 may receive user information (height, stride, gender, age, fat, etc.) through the input unit 120 and sense the user information using various sensing units included in the portable device 100, and the controller 180 may calculate a (constant) according to the properties of the user based on the user information. Meanwhile, a (constant) may be 1 and the constant of 1 may be corrected according to user information. That is, a (constant) may be changed according to user.

In addition, the controller 180 may multiply the number of steps of the user per 60 seconds by a (constant), thereby calculating the virtual heart rate.

When the virtual heart rate is calculated using the walking speed of the user, the controller 180 may compare the calculated virtual heart rate with the actual heart rate of the user measured by the second sensor 144 to evaluate the physical strength of the user. Specifically, the controller 180 may evaluate the physical strength of the user using a difference between the actual heart rate of the user and the virtual heart rate after a specific time has passed.

For example, referring to FIG. 6b, it can be seen that the actual heart rate in the period (b) of the user A is greater than the virtual heart rate calculated using the walking speed of the user. That is, the maximum value of the actual heart rate in the period (b) of the user A is greater than the virtual heart rate calculated using the walking speed of the user. In addition, when the actual heart rate of the user A is greater than the virtual heart rate calculated using the walking speed of the user by a specific value or more, cardiopulmonary capacity of the user A may be evaluated as being bad.

In the case of the user B, it can be seen that the actual heart rate of the user B is similar to the virtual heart rate calculated using the walking speed of the user. That is, the maximum value of the actual heart rate in the period (b) of the user B is similar to the virtual heart rate calculated using the walking speed of the user. In addition, when the actual heart rate of the user B is within a specific range of the virtual heart rate calculated using the walking speed of the user, cardiopulmonary capacity of the user B may be evaluated as being normal.

In the case of the user C, it can be seen that the actual heart rate of the user C is less than the virtual heart rate calculated using the walking speed of the user. That is, the maximum value of the actual heart rate in the period (b) of the user C is less than the virtual heart rate calculated using the walking speed of the user. In addition, when the actual heart rate of the user C is less than the virtual heart rate calculated using the walking speed of the user by the specific value or more, cardiopulmonary capacity of the user C may be evaluated as being good.

Meanwhile, the controller 180 may evaluate the physical strength of the user using the heart rate of the user measured for the first time.

Here, the first time may be a time from when the walking speed of the user is changed by the specific speed to when the heart-rate curve of the user is changed from rising to falling (that is, when the heart rate of the user reaches a highest heart rate).

Alternatively, the first time may be a time from when the walking speed of the user is changed by the specific speed to when the maximum value of the heart rate of the user is capable of being estimated. Here, when the maximum value of the heart rate of the user is capable of being estimated may be when a convergence value of the heart-rate curve (that is, the maximum value of the heart rate) is capable of being estimated through analysis of change in slope of the heart-rate curve.

Meanwhile, although the virtual heart rate and the actual heart rate are compared in the period (b) in which the walking speed of the user is increased to evaluate the physical strength of the user in the above-described embodiment, the virtual heart rate and the actual heart rate may be compared in the period in which the walking speed of the user is decreased to evaluate the physical strength of the user.

Specifically, if the walking speed of the user is 7 km/h in the period (b) and is 4 km/h in the period (c) and change in walking speed of the user for evaluating the physical strength of the user is 2 km/s, since the walking speed of the user is changed by the specific speed (2 km/s) or more, the controller 180 may evaluate the physical strength of the user using the heart rate of the user.

In this case, since the minimum value of the heart rate of the user A in the period (c) is greater than the virtual heart rate, the controller 180 may evaluate the cardiopulmonary capacity of the user A as being bad. As another example, since the minimum value of the heart rate of the user B in the period (c) is similar to the virtual heart rate, the controller 180 may evaluate the cardiopulmonary capacity of the user B as being normal. As another example, since the minimum value of the heart rate of the user C in the period (c) is less than the virtual heart rate, the controller 180 may evaluate the cardiopulmonary capacity of the user C as being good.

Meanwhile, although the physical strength of the user is evaluated using the slope of the heart-rate curve or the maximum value or minimum value of the heart rate in the present embodiment, the present invention is not limited thereto. For example, all methods of evaluating the physical strength of the user using change in heart rate of the user are applicable. In addition, a method of evaluating the physical strength of the user using the slope of the heart-rate curve and the maximum value of the heart rate or a method of evaluating the physical strength of the user using the slope of the heart-rate curve and the minimum value of the heart rate may be implemented.

Meanwhile, when the virtual heart rate calculated using the walking speed of the user is changed by the specific value or more as the walking speed of the user is changed by the specific speed or more, the controller 180 may evaluate the physical strength of the user.

Specifically, the controller 180 may calculate the virtual heart rate using the walking speed of the user. For example, if the constant a according to the properties of the user is 0.95 and the walking speed of the user is 84 number/minute, the virtual heart rate corresponding to the walking speed of the user may be 79.8 number/minute. In this case, when the walking speed of the user is increased such that the walking speed of the user becomes 190 number/minute, the virtual heart rate corresponding to the walking speed of the user may be 180.5 number/minute. In addition, if it is assumed that increment of the virtual heart rate for evaluating the physical strength of the user is 60, since the virtual heart rate of the user is increased from 79.8 to 180.5 by 60 or more, the controller 180 may determine that the walking speed of the user is changed by the specific speed or more and evaluate the physical strength of the user using the measured heart rate.

FIG. 7 is a graph showing heart rates of a plurality of users according to stepwise change in walking speed.

Figure 7A:
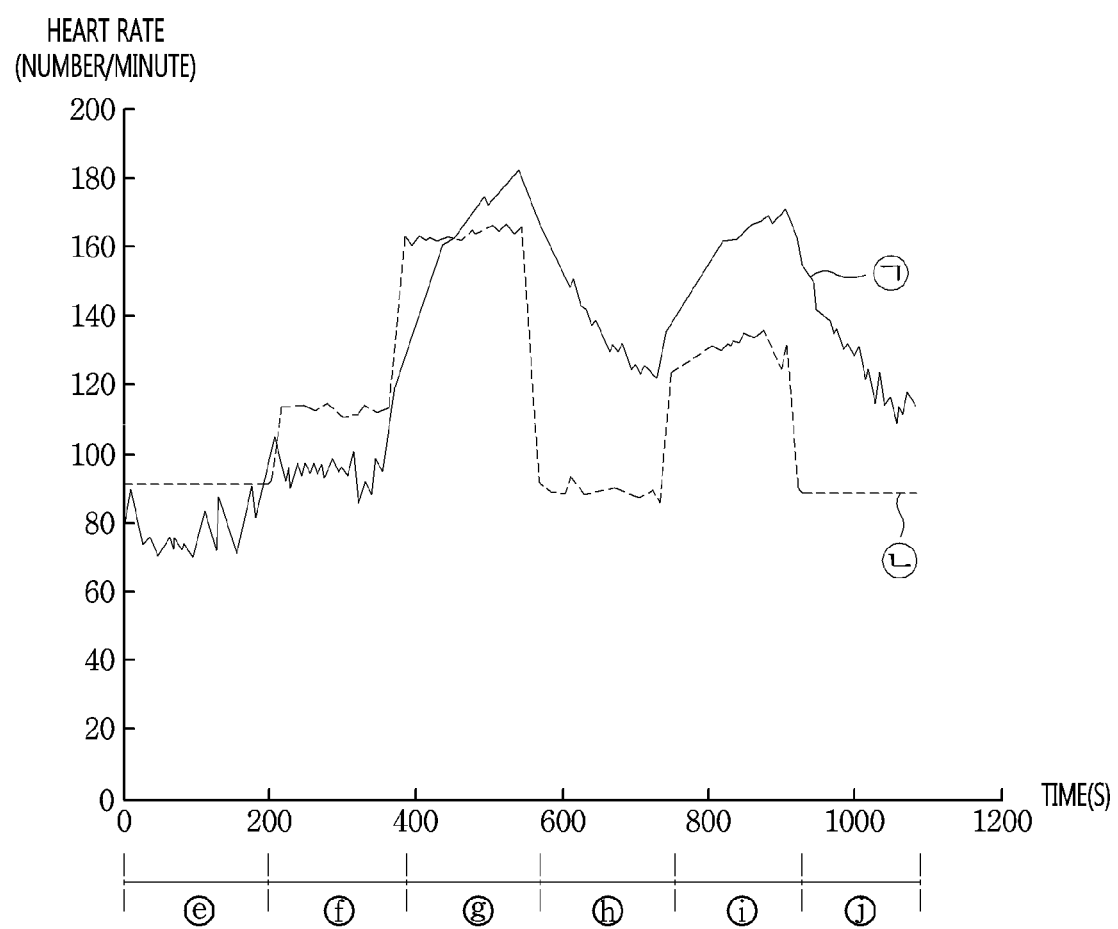
FIGS. 7a to 7c are diagrams showing a graph showing the heart rates of a plurality of users according to stepwise change in walking speed according to an embodiment of the present invention.
Figure 7B:
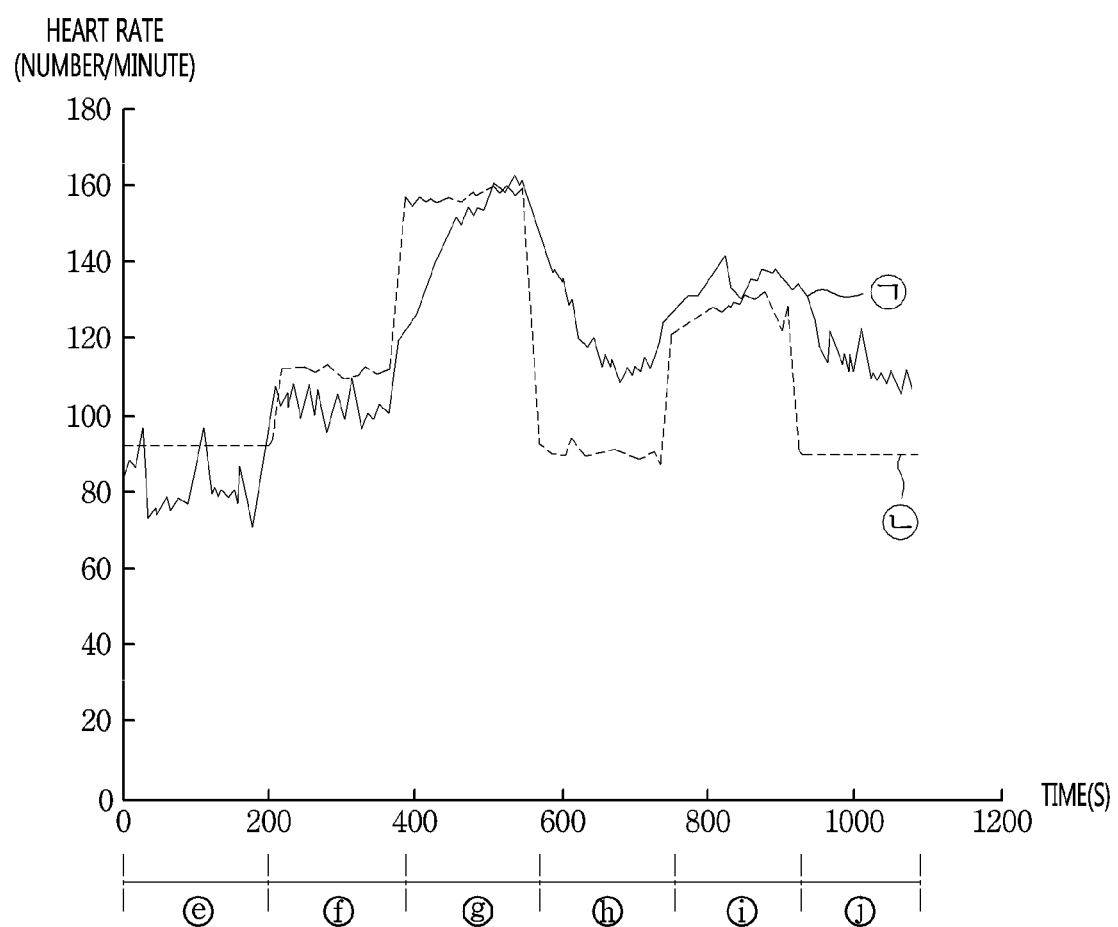
Figure 7C:
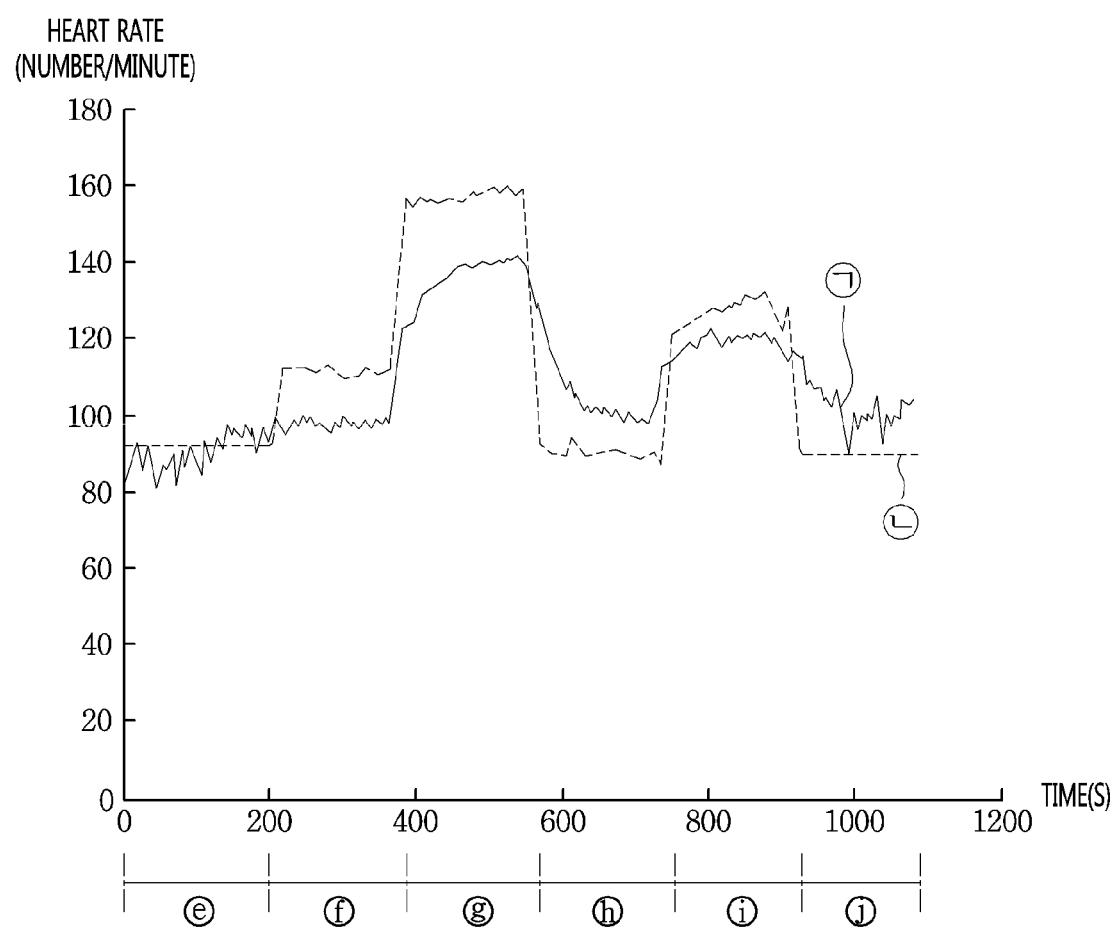

FIG. 7a is a graph showing the heart rate of the user A, FIG. 7b is a graph showing the heart rate of the user B, and FIG. 7c is a graph showing the heart rate of the user C.

Assume that the walking speed of the user which is changed to evaluate the physical strength of the user is 3 km/h.

The walking speed of the user in a period ⓔ is 3 km/h. In addition, the walking speed of the user in a period ⓕ is 5 km/h. That is, since the walking speed of the user is not changed by a specific speed (3 km/h) which is changed to evaluate the physical strength of the user, even when entering the period ⓕ, the controller 180 does not start evaluation of the physical strength of the user.

The walking speed of the user in a period ⓖ is 9 km/h. Accordingly, since the walking speed of the user is changed from 5 km/h to 9 km/h by the specific speed (3 km/h) or more, upon entering the period ⓖ, the controller 180 may start to evaluate the physical strength using the heart rate of the user.

In this case, as described with reference to FIG. 6a, the maximum heart rate of the user is compared with the maximum heart rate obtained statistically under the same condition and the slope of change in heart rate of the user is compared with that of change in heart rate obtained statistically under the same condition, thereby evaluating the physical strength of the user.

In addition, as described with reference to FIG. 6b, the maximum heart rate of the user may be compared with the virtual heart rate, thereby evaluating the physical strength of the user.

For example, in the heart rate ⓞ of the user A shown in FIG. 7a, a maximum heart rate is greater than a virtual heart rate ⓥ calculated using the walking speed of the user. In addition, if the maximum heart rate of the user is greater than the virtual heart rate by a specific value or more, the controller 180 may evaluate the physical strength of the user as being weak.

In contrast, in the heart rate ⓞ of the user B shown in FIG. 7b, a maximum heart rate is similar to a virtual heart rate ⓥ calculated using the walking speed of the user. In addition, if the maximum heart rate of the user is within a specific value range of the virtual heart rate, the controller 180 may evaluate the physical strength of the user as being normal.

In addition, in the heart rate ⓞ of the user C shown in FIG. 7c, a maximum heart rate is less than a virtual heart rate ⓥ calculated using the walking speed of the user. In addition, if the maximum heart rate of the user is less than the virtual heart rate by the specific value or more, the controller 180 may evaluate the physical strength of the user as being strong.

In addition, the controller 180 may compare the heart rate of the user in a previous period with and the heart rate of the user in a current period and evaluate the physical strength of the user. For example, in the case of the user A, since the maximum heart rate of the user in the previous period ⓕ is 100 and the maximum heart rate in the current period ⓖ is 180, a difference between the maximum heart rates is 80. In contrast, in the case of the user C, since the maximum heart rate of the user in the previous period ⓕ is 100 and the maximum heart rate in the current period ⓖ is 140, a difference between the maximum heart rates is 40. Accordingly, the controller 180 may evaluate the physical strength of the user C having smaller change in heart rate as being stronger than that of the user A.

Meanwhile, the walking speed of the user in the period ⓗ is 3 km/h. Accordingly, since the walking speed of the user is changed from 9 km/h to 3 km/h by a specific speed (3 km/h) or more, upon entering the period ⓗ, the controller 180 may start evaluation of the physical strength using the heart rate of the user.

In this case, as described with reference to FIG. 6a, the minimum heart rate of the user may be compared with a minimum heart rate obtained statistically under the same condition to evaluate the physical strength of the user, and the physical strength of the user may be evaluated using the slope of the heart-rate decreasing graph.

Specifically, referring to FIG. 7a, the slope of the heart-rate decreasing graph of the user A is less than those of the users B and C. In other words, the decrement per unit time of the heart rate of the user A is less than those of the users B and C. In this case, the controller 180 may compare the slope of the heart-rate decreasing graph with that of the statistically obtained heart-rate decreasing graph and evaluate the physical strength of the user A as being weak.

In addition, referring to FIG. 7c, the slope of the heart-rate decreasing graph of the user C is greater than those of the users A and B. In other words, the decrement per unit time of the heart rate of the user C is less than those of the users A and B. In this case, the controller 180 may compare the slope of the heart-rate decreasing graph with that of the statistically obtained heart-rate decreasing graph and evaluate the physical strength of the user A as being strong.

Meanwhile, the controller 180 may evaluate the physical strength of the user B as being normal.

In addition, in the period ⓗ, as described with reference to FIG. 6b, the minimum heart rate of the user is compared with the virtual heart rate to evaluate the physical strength of the user.

For example, in the heart rate ⓞ of the user A shown in FIG. 7a, a minimum heart rate is greater than a virtual heart rate ⓥ calculated using the walking speed of the user by 30 or more. In addition, if the minimum heart rate of the user is greater than the virtual heart rate by a first value (e.g., 30) or more, the controller 180 may evaluate the physical strength of the user as being weak.

In contrast, in the heart rate ⓞ of the user B shown in FIG. 7b, a minimum heart rate is greater than a virtual heart rate ⓥ calculated using the walking speed of the user by 20 or more. In addition, if a difference between the minimum heart rate of the user and the virtual heart rate is less than the first value (e.g., 30) but is greater than a second value (e.g., 20), the controller 180 may evaluate the physical strength of the user as being normal.

In addition, in the heart rate ⓞ of the user C shown in FIG. 7c, a difference between a minimum heart rate and a virtual heart rate ⓥ calculated using the walking speed of the user is 10. In addition, if the difference between the minimum heart rate of the user and the virtual heart rate is equal to or less than the second value (e.g., 20), the controller 180 may evaluate the physical strength of the user as being strong.

Meanwhile, the controller 180 may compare the previous and next periods of the period in which the constant speed is maintained for a predetermined time after the walking speed of the user is changed by the specific speed or more and evaluate the physical strength of the user.

Referring to FIG. 7, while the period ⓕ is switched to the period ⓖ, the walking speed of the user was changed by the specific speed or more and physical strength evaluation was performed. In this case, the controller 170 may compare the period ⓕ as the previous period of the period ⓖ with the period ⓗ as the next period of the period ⓖ and evaluate the physical strength of the user.

For example, in the case of the user A, the maximum heart rate in the period ⓕ is 100 and the minimum heart rate in the period ⓗ is 125. Meanwhile, in the case of the user C, the maximum heart rate in the period ⓕ is 100 and the minimum heart rate in the period ⓗ is 100.

As a difference in heart rate between the previous and next periods of the period in which the constant speed is maintained for a predetermined time after the walking speed of the user is changed by the specific speed or more decreases, recovery ability of the user increases. Accordingly, the recovery ability of the user C having a small difference in heart rate between the period ⓕ and the period ⓗ is good and thus the controller 170 may evaluate the physical strength of the user C as being good.

A period ⓘ refers to a period in which the walking speed of the user is increased to 7 m/s again. Since the walking speed of the user is changed from 9 km/h to 3 km/h by the specific speed (3 km/h) or more, the controller 170 may evaluate the physical strength of the user using the heart rate of the user in the period ⓘ. Meanwhile, the method of evaluating the physical strength of the user using the heart rate in the period ⓘ is equal to the method of evaluating the physical strength of the user using the heart rate in the period ⓖ, and thus a detailed description thereof will be omitted.

A period ⓙ refers to a period in which the walking speed of the user is decreased to 3 m/s again. Since the walking speed of the user is changed from 7 km/h to 3 km/h by the specific speed (3 km/h) or more, the controller 170 may evaluate the physical strength of the user using the heart rate of the user in the period ⓙ. Meanwhile, the method of evaluating the physical strength of the user using the heart rate in the period ⓙ is equal to the method of evaluating the physical strength of the user using the heart rate in the period ⓗ, and thus a detailed description thereof will be omitted.

Referring to FIG. 3 again, if the controller 180 may evaluate the physical strength of the user through analysis of the heart rate of the user, information indicating that evaluation of the physical strength of the user is possible may be output (S390).

This will be described in detail with reference to FIG. 8.

Figure 8A:
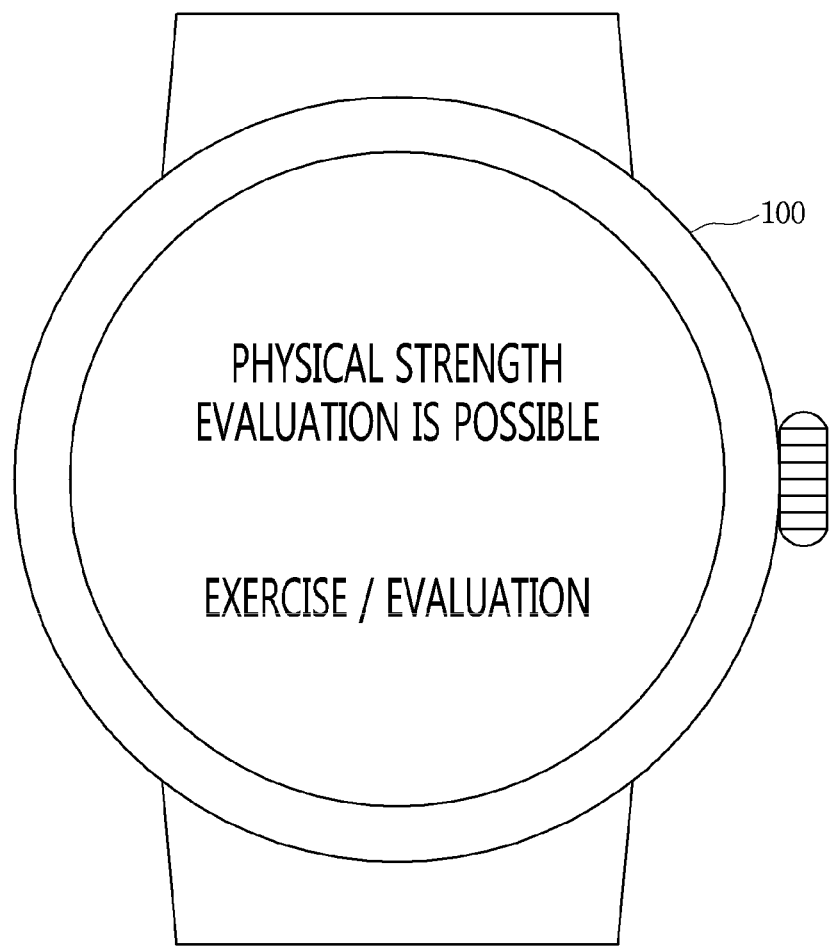
FIGS. 8a to 8c are diagrams illustrating a method of outputting information indicating that physical strength evaluation of a user is possible, according to an embodiment of the present invention.

FIG. 8a is a diagram showing a portable device, on which information indicating that physical strength evaluation of the user is possible is displayed, according to the embodiment of the present invention.

The controller 180 may output the information indicating that physical strength evaluation of the user is possible, upon determining that physical strength evaluation is possible through analysis of the heart rate of the user.

In this case, when physical strength evaluation of the user is possible through analysis of the heart rate of the user may be when a minimum time when the physical strength of the user may be evaluated using the measured heart rate of the user has passed after the walking speed of the user is changed by the specific speed or more. Here, the minimum time when the physical strength of the user may be evaluated may be a minimum time when the physical strength of the user may be evaluated using the slope of the heart-rate change curve of the user after the walking speed of the user is changed by the specific speed or more.

Alternatively, when physical strength evaluation of the user is possible through analysis of the heart rate of the user may be when the heart-rate curve of the user is changed from rising to falling (that is, the heart rate of the user reaches the maximum heart rate) after the walking speed is changed by the specific speed. Alternatively, when physical strength evaluation of the user is possible through analysis of the heart rate of the user may be when the heart-rate curve of the user is changed from falling to rising (that is, the heart rate of the user reaches the minimum heart rate) after the walking speed is changed by the specific speed.

Alternatively, when physical strength evaluation of the user is possible through analysis of the heart rate of the user may be when at least one of the maximum value and the minimum value of the heart rate of the user is predictable after the walking speed is changed by the specific speed.

Alternatively, when physical strength evaluation of the user is possible through analysis of the heart rate of the user may be an arbitrary time when physical strength evaluation of the user is possible before stoppage of change in walking speed by the specific speed or more. For example, in FIG. 7, if the walking speed of the user in the period ⓙ is 3 km/s and the walking speed of the user after the period ⓙ is 1 km/s and change in walking speed of the user by the specific speed or more is stopped, the time when physical strength evaluation of the user is possible may be one of when the period ⓖ ends, when the period ⓗ ends, the period ⓘ ends, and the period ⓙ ends.

The controller 170 may control the display 151 to display the information indicating that physical strength evaluation of the user is possible, when physical strength evaluation of the user is possible.

Meanwhile, although the information indicating that physical strength evaluation of the user is possible is output through the display 151 in the present embodiment, the present invention is not limited thereto. For example, the controller 180 may control the audio output unit 153 to audibly output the information indicating that physical strength evaluation of the user is possible. In addition, the controller 180 may control the haptic module 153 to output the information indicating that physical strength evaluation of the user is possible in a specific vibration pattern.

Meanwhile, when the minimum time when physical strength evaluation of the user is possible (the time when the slope of the increased heart-rate may be measured) has passed, the physical strength of the user can be evaluated. However, if the user continuously walks to measure a maximum heart rate or if the walking speed of the user is decreased by the specific speed or less to measure the slope of the heart rate decreasing curve and the minimum heart rate, accuracy of physical strength evaluation can be further improved.

Accordingly, the controller 170 may display a message "Physical strength evaluation can be analyzed. If desired, exercise may be continuously taken or finished." when the minimum time when physical strength evaluation of the user is possible, thereby leading additional walking of the user.

Figure 8B:
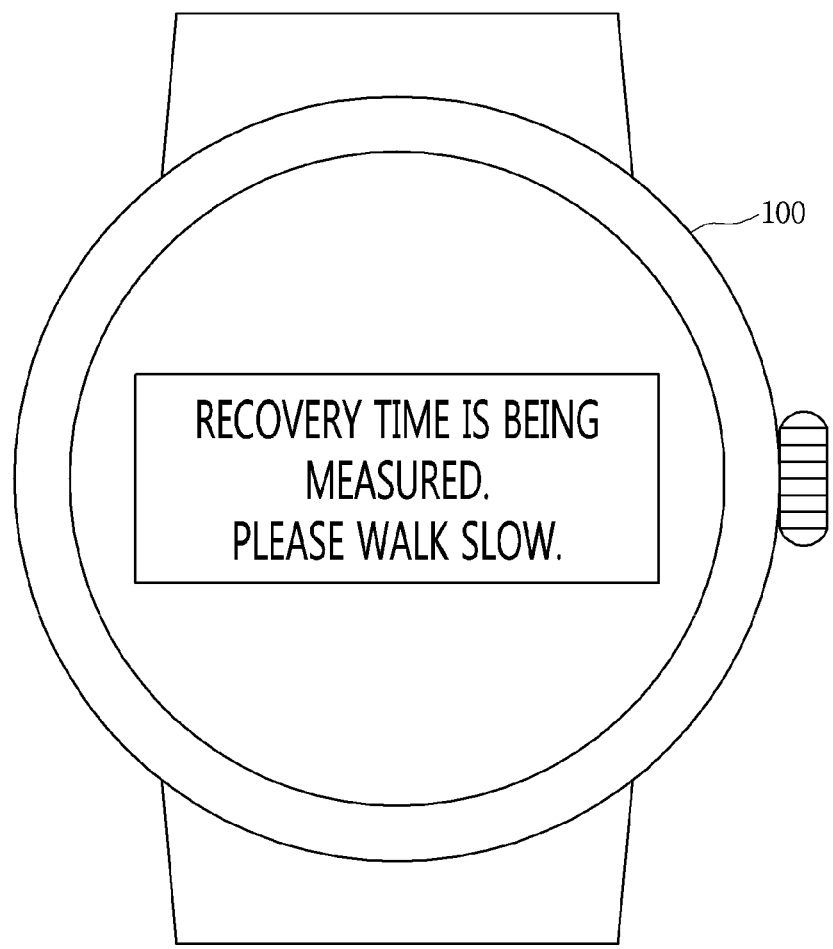

Meanwhile, the user may select an "evaluation" item in order to evaluate the physical strength thereof. When user input of evaluating the physical strength is received through the input unit 120, the controller 180 may output information for leading the user to measure the recovery ability of the user, as shown in FIG. 8b.

When the user walks in a state of decreasing the walking speed thereof according to the information, the controller 180 may measure the recovery ability of the user. In the method of measuring the recovery ability of the user, all the above-described embodiments may be used as the method of evaluating the physical strength of the user when the walking speed of the user is decreased.

Meanwhile, although the information for leading walking in order to measure the recovery ability of the user when user input of evaluating the physical strength of the user is received is output to measure the recovery ability of the user in the present embodiment, the present invention is not limited thereto. For example, the controller 180 may output the result of evaluating the physical strength of the user immediately when user input of evaluating the physical strength of the user is received.

Figure 8C:
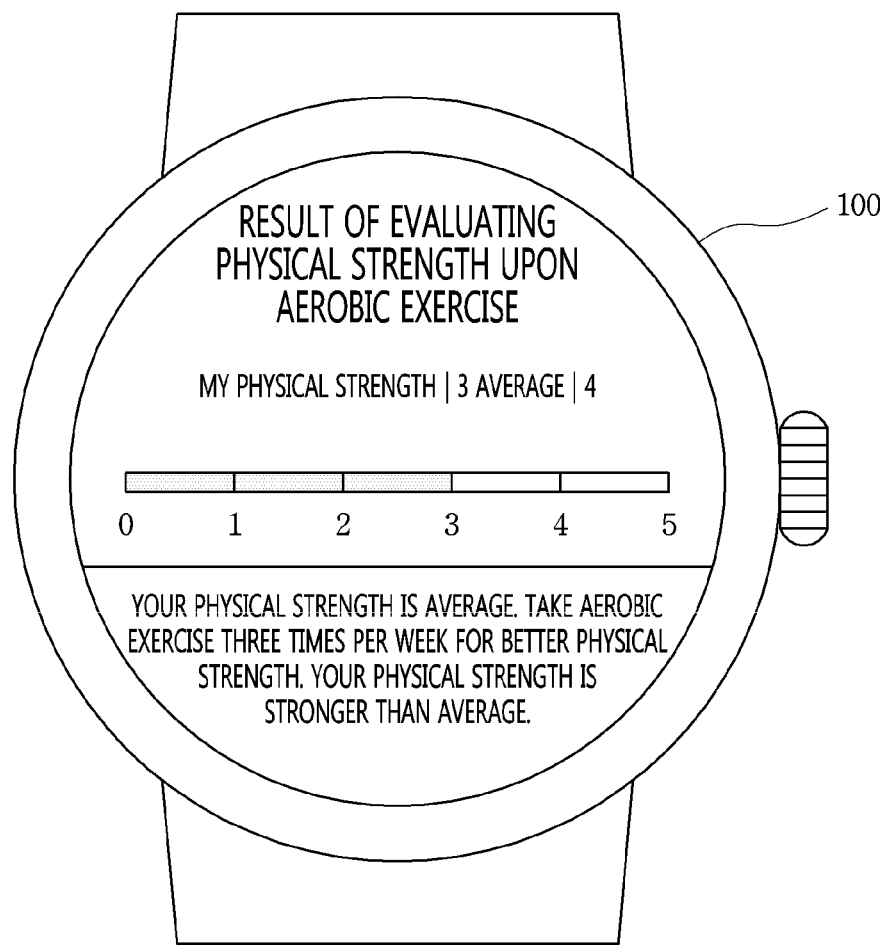

FIG. 8c is a diagram illustrating a method of outputting the result of evaluating the physical strength of the user.

In FIG. 8c, the controller 180 may display the display 151 to display the result of evaluating the physical strength of the user.

The controller 180 may display at least one of the elements for evaluating the physical strength of the user, such the maximum heart rate of the user, the minimum heart rate, heart-rate change, the recovery time of the heart rate of the user, the walking speed of the user, etc. and display a graph showing at least one of all elements considered to evaluate the physical strength of the user.

In addition, the controller 180 may display a grade corresponding to the physical strength of the user among a plurality of strength grades and display an average strength grade considering the gender and age of the user using user information.

FIG. 9 is a diagram illustrating a method of outputting an exercise guide suitable for the physical strength of a user.

In FIG. 9a, a total of 5 exercise levels and purposes and effects of the exercise per level are shown. In addition, the controller 180 may recommend exercise of a level suitable for the physical strength of the user according to physical strength evaluation.

In the table of FIG. 9a, Max HR means the maximum heart rate of the user who is taking exercise, which may be recommended to the user according to the age of the user. For example, as the age of the user increases, the maximum heart rate of the user who is taking the recommended exercise may decrease. As the age of the user decreases, the maximum heart rate of the user who is taking the recommended exercise may increase.

In the table of FIG. 9a, the exercise level may be divided according to the ratio of Max HR. For example, exercise of a first level 911 may increase the maximum heart rate of the user from 50% to 60% of Max HR and exercise of a fifth level 915 may increase the maximum heart rate of the user from 90% to 100% of Max HR. That is, if the maximum heart rate during exercise which may be recommended to a twenty-year-old user is 200, exercise of the first level 911 may increase the maximum heart rate of the user from 100 to 120 and exercise of the fifth level 915 may increase the maximum heart rate of the user from 180 to 200.

In addition, in the table of FIG. 9a, the purposes and effects of exercises of the respective levels 911, 912, 913, 914 and 915 are shown. For example, exercise of the second level 912 refers to exercise for weight loss and can burn fat and calories. As another example, exercise of the third level 913 refers to exercise for base-aerobic and can increase stamina and endurance.

Such a table may be stored in the memory 170 and used to guide exercise suitable for the physical strength of the user.

Meanwhile, although the exercise level is classified using the recommended maximum heart rate changed according to the age of the user in the present embodiment, this is merely exemplary and the exercise level may be classified using the recommended maximum heart rate considering various elements such as the height, weight, body fat and fat-free mass of the user.

In addition, although the exercise level is classified into five levels in the present embodiment, the exercise levels may be variously changed.

Although the exercise level is classified according to the ratio of the maximum heart rate recommended according to the user in the present embodiment, the present invention is not limited thereto and the exercise level may be classified in consideration of various elements for providing exercise suitable for the user.

Meanwhile, the controller 180 may display a UI for recommending exercise of a level suitable for the physical strength of the user. This will be described with reference to FIG. 9b.

Figure 9B:
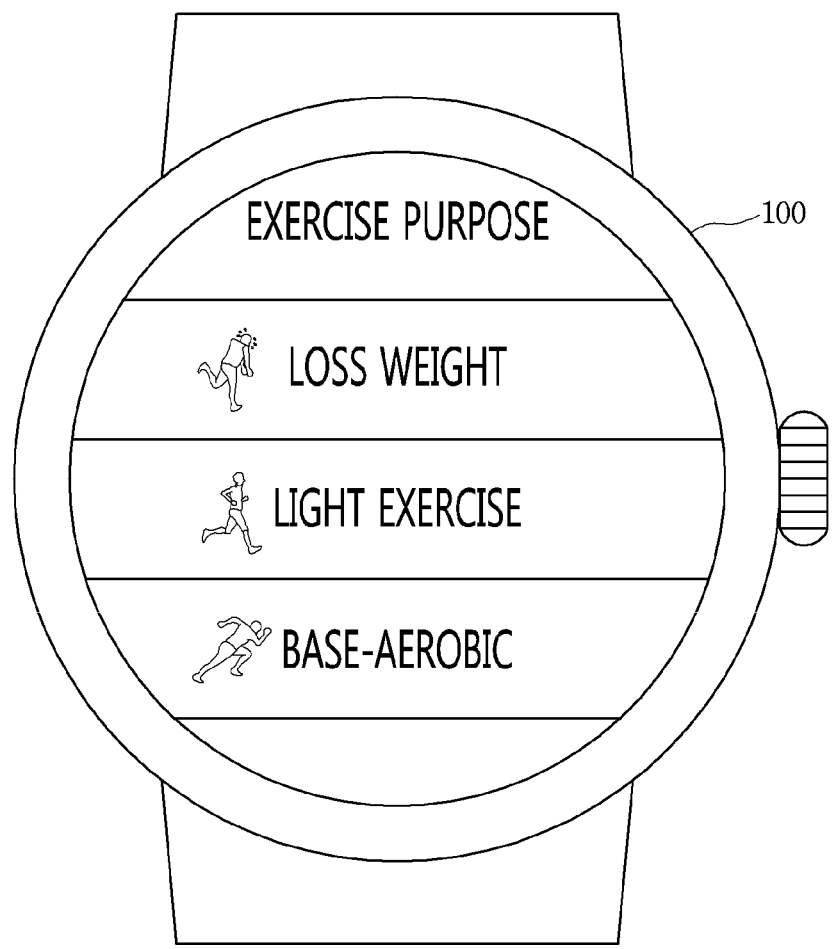

FIG. 9b is a diagram showing a screen on which a UE for recommending exercise of a level suitable for the physical strength of the user is displayed.

In FIG. 9b, the controller 180 may control the display 151 to display the UI for recommending the exercise of the level suitable for the physical strength of the user. Specifically, the controller 180 may display the UI for recommending exercise of the level corresponding to the strength grade of the user.

In addition, the controller 180 may display the UI for recommending exercise of below the level corresponding to the strength grade of the user.

For example, if the strength grade of the user is classified into five grades and the level of exercise recommended to the user is classified into five levels, exercise of the third level or less, that is, exercise of a first level, exercise of a second level and exercise of a third level may be recommended to the user having a third strength grade.

In FIG. 9b, since it is assumed that the physical strength of the user is evaluated as a third grade among a total of five grades, it can be seen that exercise "weight loss" corresponding to a first level, exercise "light exercise" corresponding to a second level and exercise "base-aerobic" corresponding to a third level may be recommended to the user. The input unit 120 may receive user input of selecting exercise suitable for the exercise purpose of the user from among exercise corresponding to the first level, exercise corresponding to the second level and exercise corresponding to the third level.

Meanwhile, although the strength grade of the user is classified into five grades and the exercise level recommended to the user is classified into five levels in the present embodiment, the present invention is not limited thereto. For example, if the strength grade of the user is classified into seven grades, the exercise level recommended to the user is classified into 10 levels and the level of exercise corresponding to the strength grade of the user having a third grade is a fourth level, the controller 180 may display a UI for recommending to exercise corresponding to a first level, a second level, a third level and a fourth level.

Figure 9C:
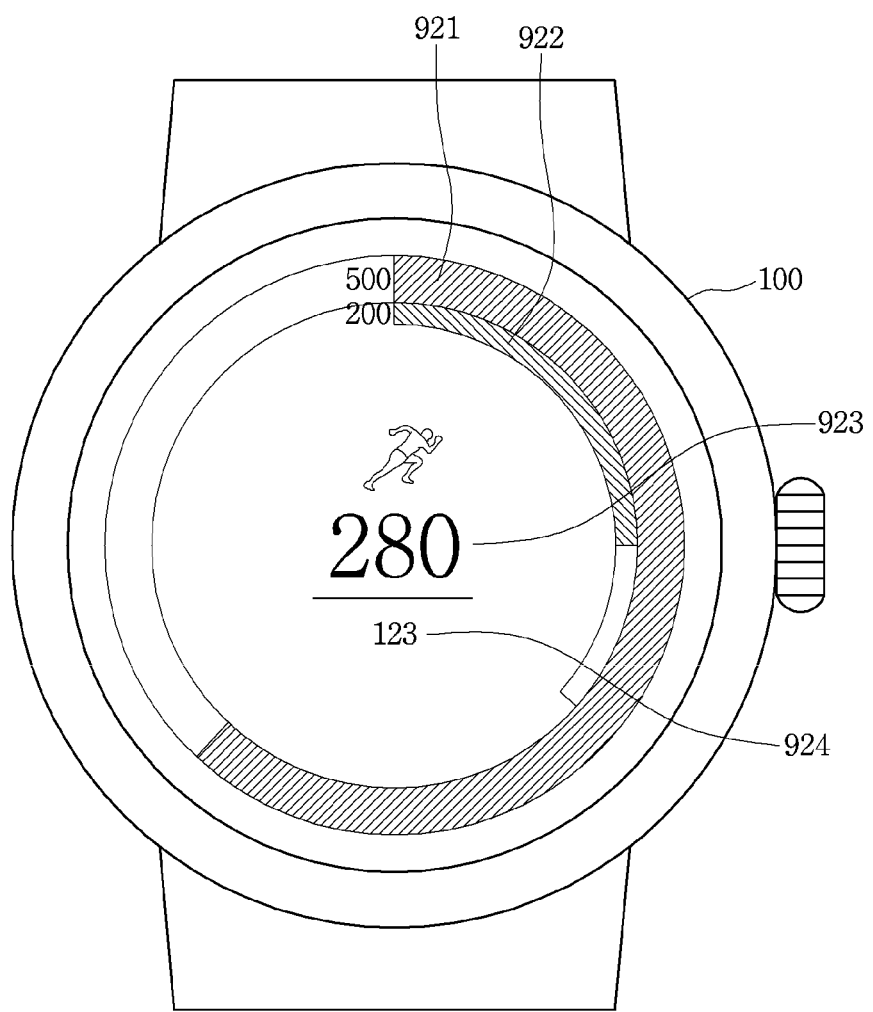

FIG. 9c is a diagram showing a UI screen on which one exercise selected by a user from among recommended exercises is displayed.

When user input of selecting one of exercises of below the level corresponding to the strength grade of the user is received, the controller 180 may output a UI for guiding exercise selected by the user. For example, the controller 180 may gauge and output a target workrate 921, a current workrate 922, target consumed calories 923 and currently consumed calories 924 according to the level of exercise selected by the user.

Figure 9D:
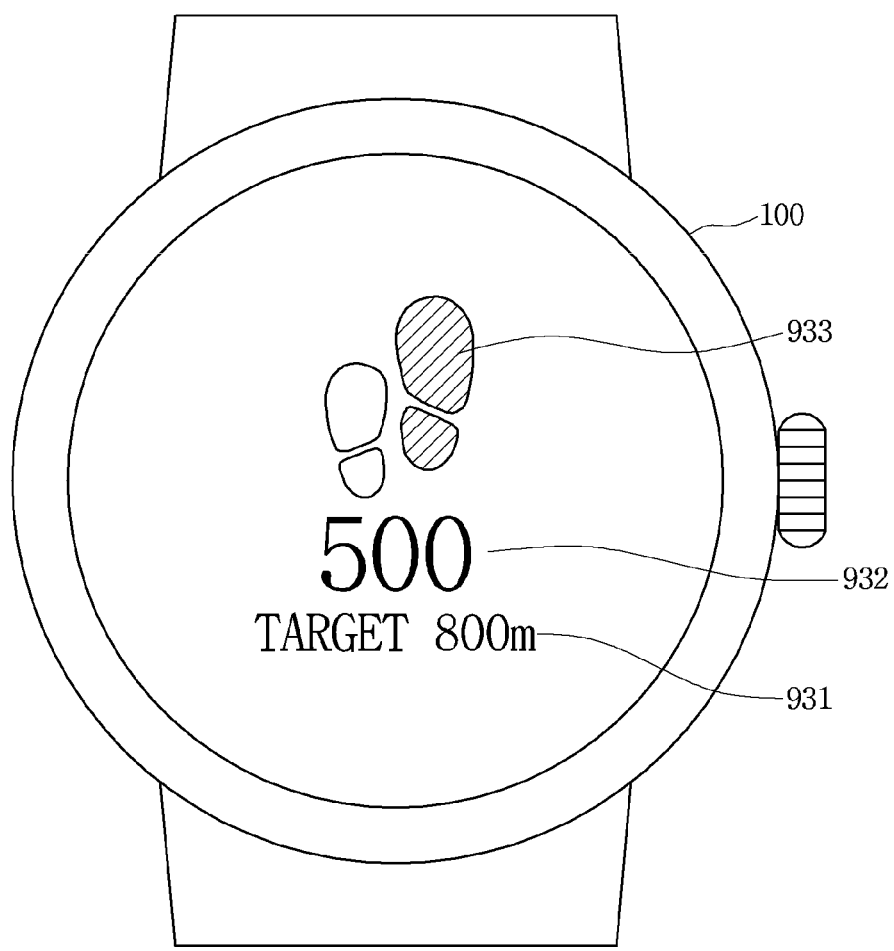

In addition, as shown in FIG. 9d, a target movement distance 931 and a current movement distance 932 according to the level of exercise selected by the user may be displayed and a UI 933 for guiding walking of the user such that the user moves the target movement distance within a specific time may be displayed.

Meanwhile, guide of exercise of the user and evaluation of the physical strength of the user may be performed in parallel. Specifically, the controller 180 may evaluate the physical strength of the user while guiding exercise selected by the user. In this case, the controller 180 may guide exercise selected by the user such that exercise of the user satisfies a criterion for evaluating the physical strength of the user described with reference to FIGS. 3 to 8. For example, the controller 180 may lead the user to walk, to change the walking speed by the specific speed or more or to maintain the speed in a state of changing the walking speed by the specific speed or more. In addition, the controller 180 may evaluate the physical strength of the user while guiding exercise selected by the user, thereby outputting the result of evaluating the physical strength.

FIG. 9e is a diagram illustrating a method of guiding exercise of a user according to another embodiment of the present invention.

In FIG. 9e, the controller 180 may display the current heart rates 941 and 943 of the user. In addition, the controller 180 may display texts 942 and 944 for guiding exercise of the user. In addition, the controller 180 may output information 955 indicating a break time of the user.

In addition, the controller 180 may provide the user with the intensity of exercise suitable for the level of exercise selected by the user by a combination of a plurality of exercise methods. For example, as shown in FIG. 9e, a plurality of exercise methods such as run, cool down and rest may be provided to the user to correspond to the intensity of exercise selected by the user. In addition, the controller 180 may provide the user with a combination of a plurality of exercise methods such that the user takes exercise in correspondence with the criterion for evaluating the physical strength of the user described with reference to FIGS. 3 to 8. Therefore, the controller 180 may evaluate the physical strength of the user while guiding exercise according to the physical strength of the user and selection of the user.

Figure 10A:
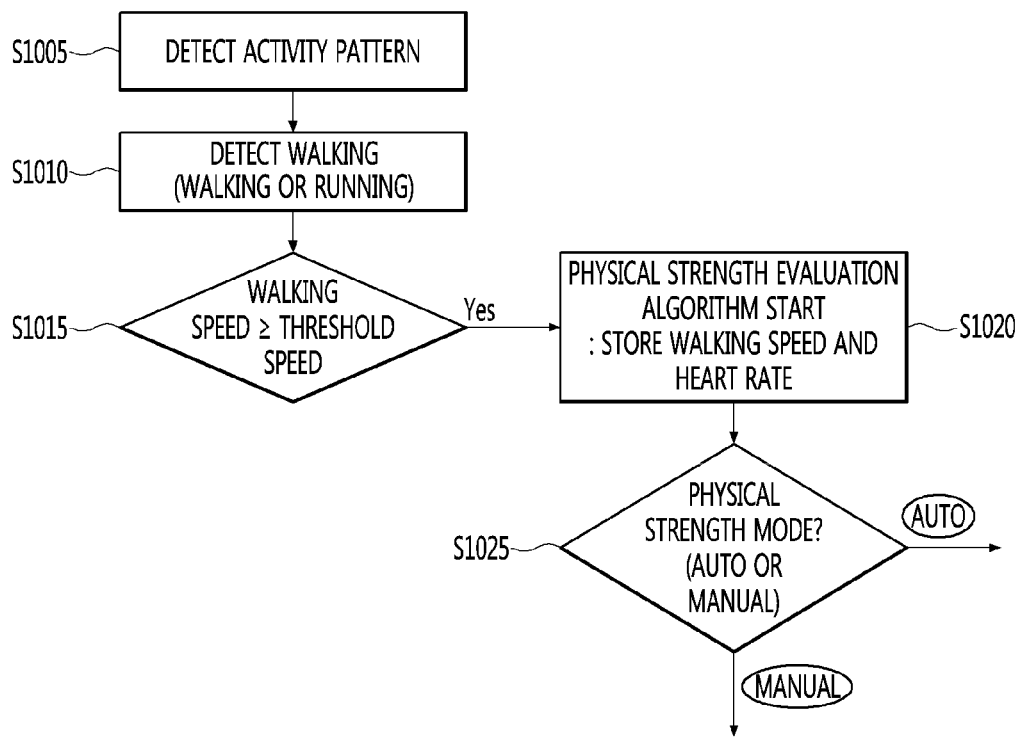
FIGS. 10a to 10c are flowcharts illustrating a physical strength evaluation method of a portable device according to an embodiment of the present invention.
Figure 10B:
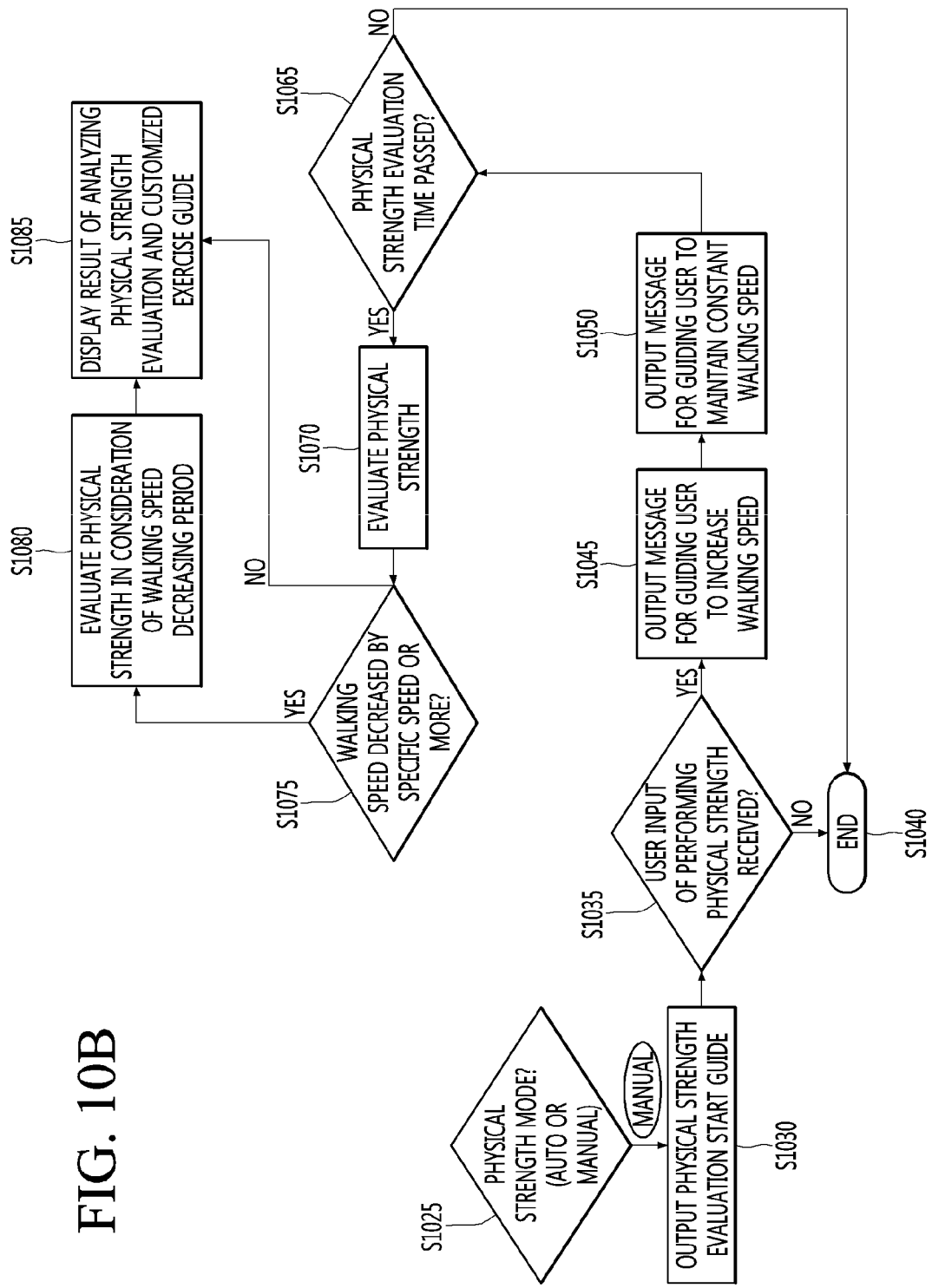
Figure 10C:
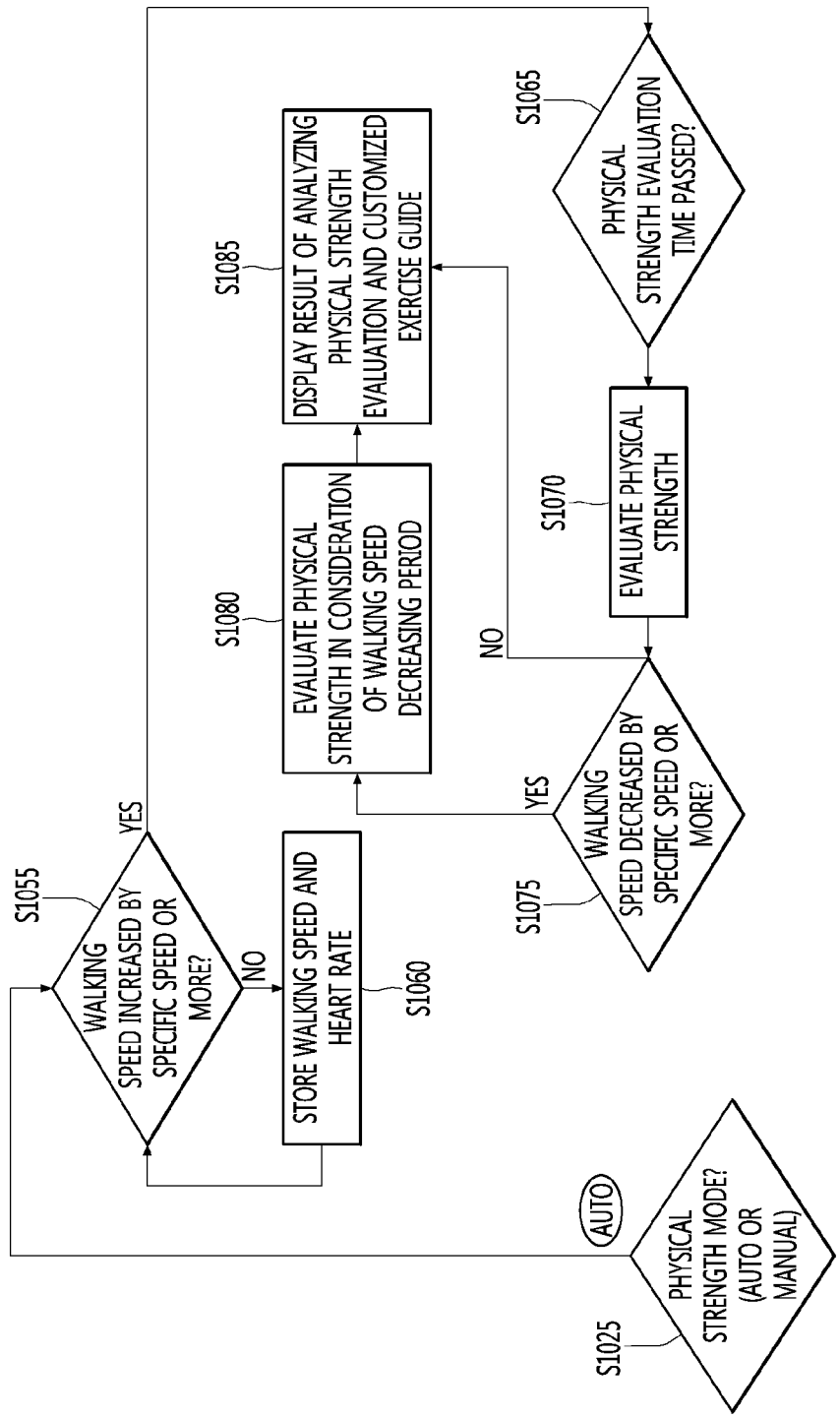

FIG. 10 is a flowchart illustrating a physical strength evaluation method of a portable device according to an embodiment of the present invention.

In FIG. 10, the portable device 100 may detect activity and activity pattern of the user through the first sensor 143 (S1005).

In addition, the controller 180 may detect that the activity of the user is walking using the sensed result of the first sensor 143 (S1010).

Meanwhile, the controller 180 may calculate the walking speed of the user using the sensed result of the first sensor 143. In addition, whether the walking speed of the user is equal to or greater than a threshold speed may be determined (S1015). Here, the threshold speed may be a minimum walking speed of the user, at which the physical strength of the user may be evaluated using the heart rate of the user.

Specifically, the threshold speed may be at least one of a movement speed of the user equal to or greater than a specific speed, the number of steps per unit time of the user equal to or greater than a predetermined number, and a speed corresponding to a virtual heart rate equal to or greater than a specific value. For example, the threshold speed may be the movement speed of the user equal to or greater than 4 km/s, the number of steps equal to or greater than 80 number/minute, and the movement speed of the user, at which the virtual heart rate equal to or greater than 70 number/minute may be calculated.

Meanwhile, the controller 180 may continuously measure the heart rate of the user before a physical strength evaluation algorithm starts. In this case, the threshold speed may be the speed corresponding to the virtual heart rate equal to or greater than the specific number from the actual heart rate while the heart rate of the user is stably maintained. For example, if the actual heart rate while the heart rate of the user is stably maintained is 70 number/minute and the specific number is 20, the threshold speed may be the movement speed of the user, at which the virtual heart rate equal to or greater than 90 number/minute may be calculated.

Meanwhile, the controller 180 may start the physical strength evaluation algorithm when the movement speed of the user is increased by the specific speed or more.

When the walking speed of the user is equal to or greater than the threshold speed, the controller 180 may start the physical strength evaluation algorithm (S1020).

When the physical strength evaluation algorithm starts, the controller 180 may start to evaluate the physical strength of the user using the walking speed of the user received from the first sensor 143 and the heart rate of the user received from the second sensor 144 and store the walking speed of the user and the heart rate of the user in the memory 170 (S1020).

Meanwhile, when the physical strength evaluation algorithm starts, the controller 180 may turn on the second sensor 144 for sensing the heart rate of the user. Specifically, in order to reduce power loss of the second sensor 144, the controller 180 may maintain the second sensor 144 for sensing the heart rate of the user in the OFF state, turn on the second sensor 144 when physical strength evaluation algorithm starts, and measure the heart rate of the user.

The controller 180 may detect that the activity of the user is walking and turn the second sensor 144 on when the walking speed of the user is equal to or greater than the threshold speed. The present invention is not limited thereto and the controller 180 may turn the second sensor 144 on by only detecting that the activity of the user is walking.

Meanwhile, the second sensor 144 may include a photoplethysmography (PPG) sensor.

Meanwhile, although the second sensor 144 is maintained in the OFF state and then the second sensor 144 is turned on when the physical strength evaluation algorithm starts in the present embodiment, the present invention is not limited thereto. Specifically, the second sensor 144 may be maintained in the ON state to continuously sense the heart rate of the user.

Meanwhile, the controller 180 may determine whether the mode for evaluating the physical strength of the user is auto or manual (S1025). Here, the mode for evaluating the physical strength of the user may be set by the default. In addition, the mode for evaluating the physical strength of the user may be automatically or manually set by user input received through the input unit 120.

The embodiment in which the physical strength evaluation mode is manually set will be described with reference to FIG. 9b.

The controller 180 may output a physical strength evaluation start guide when the mode for evaluating the physical strength of the user is manually set (S1030). For example, the controller 180 may output a message indicating "Physical strength evaluation may start when you walk at a speed faster than you do now. Would you like to evaluate your physical strength?" to lead the user to change the walking speed by the specific speed or more. Meanwhile, the controller 180 may display a physical strength evaluation start guide through the display 151, audibly output the physical strength evaluation start guide through the audio output unit 152 or output the physical strength evaluation start guide in the form of vibration through the haptic module 153.

The input unit 120 may receive user input of performing physical strength evaluation (S1035). In addition, when user input of rejecting physical strength evaluation is received through the input unit 120, the controller 180 may finish the user physical strength evaluation algorithm (S1040). Meanwhile, when user input of accepting physical strength evaluation is received through the input unit 120, the controller 180 may output a message for guiding the user to increase the walking speed (S1045).

The message for guiding the user to increase the walking speed may guide the user to increase the walking speed by the specific speed or more. For example, the controller 180 may output a notice saying "Walk at a walking speed faster than you do now." to lead the user to increase the walking speed of the user.

In addition, the message for guiding the user to increase the walking speed may lead the user to select a walking intensity. For example, the controller 180 may output a message "Select a desired intensity. (1) low intensity (fast walking), (2) middle intensity (slow running) and (3) high intensity (fast running)".

Meanwhile, the controller 180 may output a message for leading the user to maintain a constant walking speed (S1050).

Specifically, the controller 180 may output a message for leading the user to increase the walking speed to the speed corresponding to the exercise intensity selected in step S945. In addition, when the walking speed of the user is increased to the speed corresponding to the exercise intensity selected by the user, the controller 180 may output a message for guiding the user to constantly maintain the walking speed at the increased speed for a predetermined time.

In this case, the controller 180 may control the display 151 to output the message for guiding the user to constantly maintain the walking speed of the user for the predetermined time as an image. For example, the controller 180 may control the display 151 to display a UI for displaying the current walking speed of the user and the walking speed which should be maintained for physical strength evaluation in the form of a gauge. In addition, when a time when the walking speed of the user is maintained at the constant speed in order to evaluate the physical strength of the user has passed, the controller 180 may control the display 151 to display a UI indicating that the predetermined time has passed.

In addition, in this case, the controller 180 may control the audio output unit 152 to audibly output the message for guiding the user to constantly the walking speed of the user for the predetermined time. For example, the controller 180 may control the audio output unit 152 to output audio corresponding to the tempo of walking which should be maintained in order to evaluate the physical strength of the user. That is, the controller 180 may calculate the tempo of walking corresponding to the walking speed which should be maintained in order to evaluate the physical strength of the user and output audio corresponding to the tempo, thereby leading the user to walk according to the audio.

In addition, the controller 180 may control the haptic module 153 to output the message for guiding the user to constantly maintain the walking speed of the user for the predetermined time as a vibration signal, thereby leading the user to walk according to the vibration signal.

Meanwhile, the controller 180 may determine whether a physical strength evaluation time has passed (S1065).

In this case, when the predetermined physical strength evaluation time has not passed, since evaluation of the physical strength of the user is impossible, the physical strength of the user may not be evaluated (S1040).

Meanwhile, when the predetermined physical strength evaluation time has passed, the controller 180 may analyze the heart rate of the user to evaluate the physical strength of the user (S1070). In this case, the method of evaluating the physical strength of the user using the heart rate described with reference to FIGS. 6 and 7 may be used.

Meanwhile, since the predetermined physical strength evaluation time has passed, the controller 180 may evaluate the physical strength of the user in step S1070. In this case, the controller 180 may output a message indicating that physical strength evaluation of the user is possible and display the result of analyzing physical strength evaluation of the user or a customized exercise guide.

When the user walks more, since accuracy of physical strength evaluation is improved, the controller 180 may output a message for leading additional walking of the user. For example, the controller 180 may control the display 151 to display a message indicating that physical strength evaluation of the user is currently possible but the user may continuously take exercise if desired.

Meanwhile, the controller 180 may determine whether the walking speed of the user is decreased by the specific speed or more (S1075). In addition, upon determining that the walking speed of the user is decreased by the specific speed or more, physical strength evaluation may be performed in consideration of a period in which the walking speed of the user is increased and a period in which the walking speed of the user is decreased (S1080).

However, upon determining that the walking speed of the user is not decreased by the specific speed or more, since physical strength evaluation may not be performed using the heart rate after step S1070, physical strength evaluation may be performed using the heart rate of the user measured until step S1070 and the process may move to step S1085 to display a physical strength evaluation analysis result.

The controller 180 may analyze the physical strength of the user using the walking speed and heart rate of the user and control the display 151 to display the analyzed result. In addition, the controller 180 may control the display 151 to display a customized exercise guide suitable for the physical strength of the user using the result of evaluating the physical strength of the user (S1085).

Meanwhile, an embodiment in which the physical strength evaluation mode of the user is automatically set will be described with reference to FIG. 9c.

The controller 180 may continuously calculate the walking speed of the user and determine whether the walking speed of the user is increased by the specific speed or more (S1055).

Upon determining that the walking speed of the user is not increased by the specific speed or more, the controller 180 may store the walking speed of the user in the memory 170, and determine whether the walking speed of the user is increased by the specific speed or more using the stored walking speed.

In addition, the controller 180 may store the heart rate of the user in the memory 170 and may evaluate the physical strength of the user using the stored heart rate when the condition for evaluating the physical strength of the user is satisfied.

Meanwhile, when the walking speed of the user is greater than the threshold speed in step S1015, the controller 180 may determine whether the walking speed of the user is changed by the specific speed or more and evaluate the physical strength of the user. For example, if the threshold speed is 2 km/h, the specific speed for evaluating the physical strength of the user is 5 km/h and the walking speed of the user is changed from 3 km/h to 9 km/h, since the walking speed of the user is changed by 5 km/h or more, the controller 180 may evaluate the physical strength of the user.

However, the present invention is not limited thereto and the controller 180 may determine whether the walking speed of the user is changed by the specific speed or more while determining whether the walking speed of the user is increased to be equal to or greater than the threshold speed, and evaluate the physical strength of the user according to the result of determination. For example, if the threshold speed is 2 km/h, the specific speed for evaluating the physical strength of the user is 5 km/h and the walking speed of the user is changed from 1 km/h to 7 km/s, since the walking speed of the user is increased to be equal to or greater than the threshold speed and is changed by 5 km/h or more, the controller 180 may evaluate the physical strength of the user using the heart rate.

Meanwhile, when the walking speed of the user is increased by the specific speed or more, the controller 180 may return to step S1065 and determine whether the time for evaluating the physical strength of the user has passed. In addition, using the same method as the case where the physical strength evaluation mode of the user is manually set, the physical strength of the user may be evaluated (S1065, S1070, S1075, S1080, S1085). However, in the auto mode, since walking of the user is automatically detected to perform physical strength evaluation without a guide, the controller 180 may not output a message indicating that physical strength evaluation of the user is possible.

Meanwhile, although the message for leading the user to walk is output when the physical strength evaluation mode is manual in the present embodiment, the present invention is not limited thereto. Specifically, the controller 170 may output at least one of a physical strength evaluation start guide, a walking speed increase guide and a constant walking speed maintenance guide to lead the user to perform physical strength evaluation, even when the physical strength evaluation mode is set to auto.

Meanwhile, although the portable device is a watch-type mobile terminal of wearable devices in the above embodiment, the portable device may be a general mobile terminal, that is, a mobile phone.

In addition, when the wearable device linked to the mobile terminal senses heartbeat and walking of the user and transmits the sensed result to the mobile terminal, the mobile terminal may measure and analyze the heart rate and walking speed of the user and evaluate the physical strength of the user. This will be described in detail with reference to FIG. 11.

Figure 11:
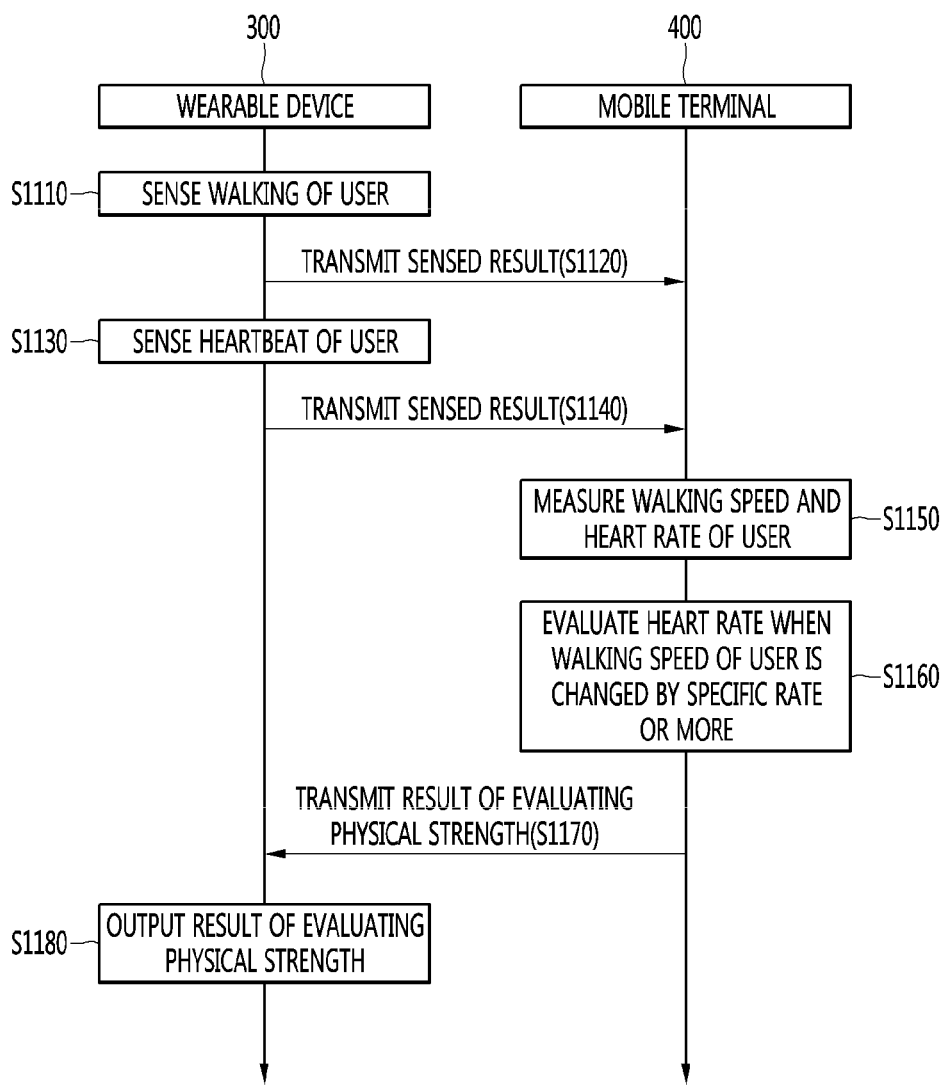
FIG. 11 is a flowchart illustrating a user physical strength evaluation method using a wearable device and a mobile terminal according to another embodiment of the present invention.

FIG. 11 is a flowchart illustrating a user physical strength evaluation method using a wearable device and a mobile terminal.

The wearable device 300 may include a first sensor for sensing walking of a user, a second sensor for sensing heartbeat of the user, a communication unit for communicating with the mobile terminal, a display for outputting a result of evaluating the physical strength of the user and a controller for controlling of operation of the wearable device.

The wearable device 300 may sense walking of the user using the first sensor (S1110). In addition, the controller of the wearable device 300 may transmit a first sensed result of sensing walking of the user to the mobile terminal 400 through the communication unit of the wearable device 300 (S1120).

The wearable device 300 may sense heartbeat of the user using the second sensor (S1130). In addition, the controller of the wearable device 300 may transmit a second sensed result of sensing heartbeat of the user to the mobile terminal 400 through the communication unit of the wearable device 300 (S1140).

The mobile terminal 400 may include all the components of the portable device described with reference to FIG. 1.

The mobile terminal 400 may receive the first sensed result and the second sensed result through the communication unit 110, and the controller 180 of the mobile terminal 400 may measure the walking speed of the user and the heart rate of the user using the received results (S1150).

In addition, the controller 180 of the mobile terminal 400 may evaluate the physical strength of the user using the walking speed of the user and the heart rate of the user (S1160).

The detailed method of measuring the walking speed of the user and the heart rate of the user and evaluating the physical strength of the user is equal to the above-described method and a detailed description thereof will be omitted.

The controller 180 of the mobile terminal 400 may transmit at least one of the result of evaluating the physical strength of the user and a customized exercise guide to the wearable device 300 through the communication unit 110 (S1170).

Meanwhile, the wearable device 300 may control the display to output at least one of the result of evaluating the physical strength of the user and the customized exercise guide (1180).

Meanwhile, although the wearable device 300 senses walking of the user, senses the heartbeat of the user and displays the result of evaluating the physical strength and the mobile terminal 400 measures the walking speed of the user, measures the heart rate of the user and evaluates the physical strength of the user in the present embodiment, the present invention is not limited thereto.

For example, the wearable device 300 may sense walking of the user, sense the heartbeat of the user, measure the walking speed of the user, measure the heart rate of the user and transmit the measured result to the mobile terminal 400 and the mobile terminal 400 may only evaluate the physical strength of the user. Alternatively, the wearable device 300 may evaluate the physical strength of the user and transmit the physical strength evaluation result to the mobile terminal 400 and the mobile terminal 400 may only display the physical strength evaluation result.

Meanwhile, the controller 180 generally serves to control the device and may be used interchangeably with a central processing unit, a microprocessor, a processor, etc.

The present invention mentioned in the foregoing description may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal. The foregoing embodiments are merely exemplary and are not to be considered as limiting the present disclosure. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments. As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

What is claimed is:

1. A physical strength evaluation method of a portable device, the method comprising:
   measuring a walking speed of a user;
   measuring a heart rate of the user; and
   evaluating a physical strength of the user using the measured heart rate when the walking speed of the user is changed by a specific speed or more by comparing a virtual heart rate with the measured heart rate,
   wherein the virtual heart rate is calculated using the walking speed of the user and a constant changed according to properties of the user, and
   wherein the constant is calculated according to the properties of the user based on user information comprising at least one of a height, a stride, a gender, an age, or a fat amount.

2. The method according to claim 1, wherein the evaluating of the physical strength of the user includes evaluating the physical strength of the user using the measured heart rate, when a constant speed is maintained for a first time after the walking speed of the user is changed by the specific speed or more.

3. The method according to claim 1,
   wherein the evaluating of the physical strength of the user includes evaluating the physical strength of the user using a slope of change in the heart rate of the user when a second time has passed after the walking speed of the user is changed by the specific speed or more, and
   wherein the second time is a minimum time when the physical strength of the user is capable of being evaluated using the measured heart rate.

4. The method according to claim 1, wherein the evaluating of the physical strength of the user includes comparing at least one of a maximum value and a minimum value of the heart rate measured for a first time after the walking speed of the user is changed by the specific speed or more with the virtual heart rate calculated using the walking speed of the user.

5. The method according to claim 1, wherein the evaluating of the physical strength of the user includes evaluating the physical strength of the user, when the virtual heart rate calculated using the walking speed of the user is changed by a specific number or more as the walking speed of the user is changed by the specific speed or more.

6. The method according to claim 1,
   wherein the evaluating of the physical strength of the user includes evaluating the physical strength of the user using the heart rate of the user measured until a first time has passed after the walking speed is changed by the specific speed, and
   wherein the method further includes outputting information indicating that evaluation of the physical strength of the user is possible when the first time has passed after the walking speed is changed by the specific speed.

7. The method according to claim 1, further comprising outputting information for guiding the user to walk,
   wherein the information for guiding the user to walk is at least one of:
   information for guiding the user to change the walking speed of the user by the specific speed or more,
   information for guiding the user to maintain the walking speed of the user at a constant speed, or
   information for guiding the user to maintain the walking speed of the user at the constant speed for a specific time.

8. The method according to claim 1, further comprising sensing walking of the user,
   wherein the measuring of the heart rate of the user includes measuring the heart rate of the user when walking of the user is sensed or when the walking speed of the user is equal to or greater than a threshold speed.

9. The method according to claim 1, wherein the virtual heart rate is calculated using the following equation:

$$\text{virtual heart rate} = a(\text{constant}) * \text{a number of steps of the user/minute}.$$

10. The method according to claim 9, wherein a default value of the constant is 1 and changeable according to the user information.

11. A portable device comprising:
    a first sensor for sensing walking of a user;
    a second sensor for sensing heartbeat of the user; and
    a controller for:
    measuring a walking speed of the user using a sensed result of the first sensor;
    measuring a heart rate of the user using a sensed result of the second sensor; and
    evaluating a physical strength of the user using the measured heart rate when the walking speed of the user is changed by a specific speed or more by comparing a virtual heart rate with the measured heart rate,
    wherein the virtual heart rate is calculated using the walking speed of the user and a constant changed according to properties of the user, and
    wherein the constant is calculated according to the properties of the user based on user information comprising at least one of a height, a stride, a gender, an age, or a fat amount.

12. The portable device according to claim 11,
    wherein the controller evaluates the physical strength of the user using a slope of change in the heart rate of the user when a first time has passed after the walking speed of the user is changed by the specific speed or more, and
    wherein the first time is a minimum time when the physical strength of the user is capable of being evaluated using the measured heart rate.

13. The portable device according to claim 11, wherein the controller turns the second sensor on when walking of the user is sensed through the first sensor or when the walking speed of the user is equal to or greater than a threshold speed.

14. A physical strength evaluation method of a portable device communicating with a wearable device, the method comprising:
  receiving a first sensed result of sensing walking of a user from the wearable device;
  receiving a second sensed result of sensing heartbeat of the user from the wearable device;
  measuring a walking speed of the user using the first sensed result;
  measuring a heart rate of the user using the second sensed result; and
  evaluating a physical strength of the user using the measured heart rate when the walking speed of the user is changed by a specific speed or more by comparing a virtual heart rate with the measured heart rate,
  wherein the walking speed of the user is calculated using at least one of a walking period of the user, a number of samples detected per specific number of steps, or a number of steps of the user detected for a specific time, and
  wherein the virtual heart rate calculated using the walking speed of the user and a constant changed according to properties of the user.

* * * * *